United States Patent [19]

Hovancik et al.

[11] Patent Number: 5,869,471
[45] Date of Patent: Feb. 9, 1999

[54] METHODS FOR THE TREATMENT OF ARTHRITIS USING PHOSPHONATES AND NSAIDS

[75] Inventors: Kristine Hovancik, Binghamton, N.Y.; Marion David Francis, Cincinnati; Richard Allen Underwood, Hamilton, both of Ohio

[73] Assignee: The Proctor & Gamble Company, Cincinnati, Ohio

[21] Appl. No.: 479,787

[22] Filed: Jun. 7, 1995

Related U.S. Application Data

[63] Continuation of Ser. No. 212,376, Mar. 11, 1994, abandoned, which is a continuation of Ser. No. 906,726, Jun. 30, 1992, abandoned.

[51] Int. Cl.$^6$ .......................... A61K 31/615; A61K 31/19
[52] U.S. Cl. ............................................. 514/166; 514/570
[58] Field of Search .................................... 514/166, 570

[56] References Cited

U.S. PATENT DOCUMENTS

| | | | |
|---|---|---|---|
| 3,676,554 | 7/1972 | McGusty et al. | 424/198 |
| 3,887,707 | 6/1975 | Sutton et al. | 424/210 |
| 4,216,212 | 8/1980 | Flora et al. | 424/204 |
| 4,264,582 | 4/1981 | Flora et al. | 424/204 |
| 4,269,828 | 5/1981 | Flora et al. | 424/204 |
| 4,275,059 | 6/1981 | Flora et al. | 424/204 |
| 4,282,214 | 8/1981 | Flora et al. | 424/204 |
| 4,330,530 | 5/1982 | Baker | 424/131 |
| 4,687,768 | 8/1987 | Benedict et al. | 514/102 |
| 4,746,654 | 5/1988 | Breliere et al. | 514/108 |
| 4,868,164 | 9/1989 | Ebetino et al. | 514/80 |
| 4,876,247 | 10/1989 | Barbier et al. | 514/89 |
| 4,939,130 | 7/1990 | Jaeggi et al. | 514/94 |
| 4,939,131 | 7/1990 | Benedict et al. | 514/102 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |

FOREIGN PATENT DOCUMENTS

| | | |
|---|---|---|
| A-26738/88 | 6/1989 | Australia . |
| A-45467/89 | 5/1990 | Australia . |
| 0100718 | 2/1984 | European Pat. Off. . |
| 0170228 | 2/1986 | European Pat. Off. . |
| 0186405 | 7/1986 | European Pat. Off. . |
| 0298553 | 1/1989 | European Pat. Off. . |
| 4011777 | 10/1990 | Germany . |

OTHER PUBLICATIONS

Forys, Victor A., "Etidronate and Osteoarthritis" (Letter to the Editor), Jama 265(21):2807 (Jun. 5, 1991).

McGuire, Mary K.B., "Biochemical Mechanisms in Arthritis", Sep. 1981, p. 265 (Thesis submitted to the University of Sheffield).

Ralston, Stuart H., "Clinical, biochemical, and radiographic effects of aminohydroxpropylidene bisphosphonate treatment in rheumatoid arthritis", *Ann. Rheum. Diseases* 48(5), pp. 396–399 (May 1989).

Heynen, G., et al., Diphosphonates and Rheumatoid Arthritis (RA), *Abstracts. ILAR XVth International Congress of Rheumatology,* Paris, France, Jun. 21–27, 1981, Rev. Rhum. Mal. Osteoartic., Special Number: 139 (Jun. 1981).

Lane, Nancy, et al., "Effect of Naproxen on Cancellous Bone in Ovariectomized Rats", *Journal of Bone and Mineral Research,* vol. 5, No. 10 (1990).

Kimmel, D.B., et al., "Long–Term Effect of Naproxen on Cancellous Bone in Ovariectomized Rats", *Bone,* 13, pp. 167–172 (1992).

Francis, M.D., et al., "The Effects of Disodium Ethane–1–Hydroxy–1,1–Diphosphonate on Adjuvant Induced Arthritis in Rats", *Calcif. Tissue Res. 9,* pp. 109–121 (1972).

Bird, H.A., et al., "A clinical and biochemical assessment of etidronate disodium in patients with active rheumatoid arthritis", *Clin. Rheumatol.* 7(1), pp. 91–94 (1988).

Flora, L., "Comparative Antiinflammatory and Bone Protective Effects of Two Diphosphonates in Adjuvant Arthritis", *Arthritis and Rheumatism,* vol. 22, No. 4, pp. 340–346 (Apr. 1979).

Couchman, K.G., et al., "The effect of anti–rheumatic drugs on factors from porcine synovium inducing chondrocyte mediated cartilage degradation", *Agents and Actions,* vol. 19 (1–2), pp. 116–122 (Oct. 1986).

Movsowitz, C., et al., "The bisphosphonate 2–PEBP inhibits cyclosporin A induced high–turnover osteopenia in the rat", *J. Lab. Clin. Med.* 115(1), pp. 62–68 (Jan. 1990).

*Primary Examiner*—Raymond Henley, III
*Attorney, Agent, or Firm*—Karen F. Clark; Mary Pat McMahon; William J. Winter

[57] ABSTRACT

The present invention provides methods of treating a human or other animal subject afflicted with arthritis, including rheumatoid, arthritis and osteoarthritis, comprising a sixty (60)-day treatment period, comprised of an optional NSAID administration regimen and a phosphonate administration regimen, wherein (a) said optional NSAID administration regimen which comprises the administration to said subject of NSAIDs at a level of from 20% to 80%, preferably 20% to 70%, most preferably 20% to 50% of the conventionally prescribed daily dose on each day that said NSAID is administered; provided that said NSAID is administered in sufficient quantities and on a sufficient number of days to alleviate symptoms of inflammation, and wherein (b) said phosphonate administration regimen comprises the administration to said subject of a phosphonate at a dose equivalent to a systemic level of from about 0.0005 mgP/kg to about 1.0 mgP/kg per day that said phosphonate is administered; provided that said phosphonate is administered at least 1 day of every said sixty (60)-day treatment period.

24 Claims, No Drawings

METHODS FOR THE TREATMENT OF ARTHRITIS USING PHOSPHONATES AND NSAIDS

This is a continuation of application Ser. No. 08/212,376, filed on Mar. 11, 1994 abandoned, which is a continuation of Ser. No. 07/906,726, filed on Jun. 30, 1992, now abandoned.

BACKGROUND OF THE INVENTION

This invention relates to methods for the treatment of arthritis, including both rheumatoid arthritis and osteoarthritis. In particular, this invention relates to such methods of treatment by the administration of bone-active phosphonate compounds and non-steroidal anti-inflammatory drugs (NSAIDs). The bone-active phosphonates and NSAIDS act in synergy with one another and their administration results in a reduction of inflammation, but also inhibits the destruction of bone and hard tissue in the intraarticular area of the joint, which permits repair of the sub-chondral bone and hard tissue.

Bone loss, or alteration in bone turnover, can result from, or be associated with, many types of arthritis, including rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial membrane and fluid. Rheumatoid arthritis symptoms include systemic weakness, fatigue, localized pain, and stiffness, weakness, swelling, and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation of the synovial cells that allow an influx of plasma proteins and cellular elements into the joint and 2) a chronic inflammatory phase occurring in the sub-synovium and sub-chondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs (NSAIDs). NSAID treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

On the other hand, osteoarthritis is an inherently non-inflammatory disorder of the movable joints characterized by deterioration and abrasion of articular cartilage, as well as by formation of new bone at the joint periphery. As osteoarthritis progresses, the surface of the articular cartilage is disrupted and wear-particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening and painful movement.

Common symptomatic treatments for osteoarthritis include analgesics, anti-inflammatories, disease-modifying arthritic drugs ("DMARDs"), steroids, and physical therapy.

A variety of polyphosphonic acid derivatives have been proposed for use in the treatment and prophylaxis of diseases involving abnormal calcium and phosphate metabolism. For example, numerous references disclose compositions containing polyphosphonates, in particular bisphosphonates, such as 1-hydroxyethylidene-diphosphonic acid ("EHDP"), and their use in inhibiting anomalous deposition and mobilization of calcium and phosphate in animal tissue: U.S. Pat. Nos. 3,683,080, issued Aug. 8, 1972 and 4,230,700, issued Oct. 28, 1980, both to Francis, and U.S. Pat. No. 4,868,164 to Ebetino, issued Sep. 19, 1989. Numerous other references describe substituted phosphonic acids useful for the treatment of osteoporosis and/or arthritis: U.S. Pat. Nos. 5,071,840 to Ebetino, et al, issued Dec. 10, 1991, 4,868,164, to Ebetino, et al., issued Sep. 19, 1989; 5,104,863, to Benedict, et al., issued Apr. 14, 1992; 4,267,108, to Blum et al., issued May 12, 1981; European Patent Application Publication No. 170,228, of Boehringer Mannheim GmbH, published Feb. 5, 1986; European Patent Application Publication No. 298,553, of Ebetino, published Jan. 11, 1989; U.S. Pat. Nos. 4,754,993, to Bosies, et al., issued Nov. 15, 1988; 4,939,130 to Jaeggi, et al., issued Jul. 3, 1990; 4,971,958 to Bosies, et al., issued Nov. 20, 1990; WO 90/12017 to Dunn, et al., published Oct. 18, 1990; WO 91/10646 to Youssefyeh, R., et al., published Jul. 25, 1991; AU-A-26738/88 to Jaeggi, K. A., publication date Jun. 15, 1989; AU-A-45467/89 of Ciba-Geigy, publication date May 31, 1990.

Suitable phosphonate compounds for use herein include those compounds described in the following references, all incorporated by reference herein: European Patent Application Publication No. 186,405, of Benedict and Perkins, published Jul. 2, 1986; sulfur-containing phosphonate compounds described in U.S. Patent to Breliere, et al., issued May 24, 1988; U.S. Pat. No. 4,876,247 to Barbier, et al., issued Oct. 24, 1989; European Patent Application Publication No. 100,718, of Breliere S. A., published Feb. 15, 1984; and those quaternary-nitrogen-continuing phosphonate compounds described in U.S. Pat. No. 4,208,401, Bauman (assigned to Colgate-Palmolive Co.), issued Jun. 17, 1980; and DE 40 11 777, Jaeggi, K., disclosed Oct. 18, 1990.

NSAIDs have been widely used in arthritis therapy for several years. The following references hereby incorporated by reference herein, describe various NSAIDs suitable for use in the invention described herein, and processes for their manufacture: U.S. Pat. No. 3,558,690 to Sallmann and Pfister, (assigned to Ciba Geigy), issued 1971; U.S. Pat. No. 3,843,681 (assigned to American Home Products), issued 1974; U.S. Pat. No. 3,766,263 to Godfrey, (assigned to Reckitt and Colman) issued 1973; U.S. Pat. No. 3,845,215 to Godfrey (assigned to Reckitt and Colman) issued 1974; U.S. Pat. No. 3,600,437 to Marshall (assigned to Eli Lilly), issued 1971; U.S. Pat. No. 3,228,831 to Nicholson and Adams, (assigned to Boots Pure Drug), issued 1966; (U.S. Pat. No. 3,385,886 to Nicholson and Adams, (assigned to Boots Pure Drug) issued 1968; U.S. Pat. No. 3,161,654 to Shen, (assigned to Merck & Co.), issued 1964; U.S. Pat. No. 3,904,682 to Fried and Harrison, (assigned to Syntex), issued 1975; U.S. Pat. No. 4,009,197 to Fried and Harrison, (assigned to Syntex), issued 1977; U.S. Pat. No. 3,591,584 to Lombardino (assigned to Pfizer) issued 1971; U.S. Pat. No. 5,068,458 to Dales et al., (assigned to Beecham Group, PLC.), issued Nov. 26, 1991; U.S. Pat. No. 5,008,283 to Blackburn et al. (assigned to Pfizer, Inc.), issued Apr. 16, 1991; and U.S. Pat. No. 5,006,547 to Loose (assigned to Pfizer), issued Apr. 9, 1991.

The administration of NSAIDs and bone-active phosphonates has been suggested as a method for enhancing the anti-inflammatory activity of NSAIDs. Such treatments using bisphosphonates and NSAIDs are disclosed in the following references, all hereby incorporated by reference herein, U.S. Pat. Nos. 4,269,828, to Flora, et al. issued May 26, 1981; 4,216,212, to Flora, et al., issued Aug. 5, 1980; 4,264,582 to Flora, et al., issued Apr. 28, 1981, 4,282,214, Flora, et al., issued Aug. 4, 1981.

Applicant has found that the administration of bone-active phosphonates and NSAIDs not only results in a reduction of inflammation, but also inhibits the destruction of bone and hard tissue in the intraarticular area of the joint, allows repair of the subchondral bone, and maintains and/or increases the range of motion of the joints. The NSAID active agent and the phosphonate active agent act in synergy. Accordingly, the benefits gained in the treatment of arthritis when utilizing the methods described herein are greater than is seen with either active agent, or their sum, if administered alone. The present methods result in a reduction in the amount of NSAIDS being administered to an arthritic patient, and in addition, also allow a reduction in the dosage of the phosphonate administered over time. The methods of this invention provide effective methods of treating arthritis, including osteoarthritis and rheumatoid arthritis, with reduced side effects compared to such methods known in the art.

SUMMARY OF THE INVENTION

The present invention provides methods of treating arthritis which inhibit intraarticular bone and joint destruction, reduce inflammation in a human or other animal subject afflicted with arthritis, and allow repair of the subchondral bone. The two active agents utilized in the methods of treatment described herein act in synergy with one another: the relief of inflammation and the inhibition of intraarticular destruction is greater when the NSAID and phosphonate are utilized in a treatment regimen together than the sum of those benefits when either of the active agents are administered alone. Accordingly, said method of treatment for arthritis significantly reduces the therapeutic dosage of NSAIDS administered, and thereby decreases or alleviates undesirable side effects associated with NSAID therapy. In addition, said therapy may also substantially reduce the dosage of the bone active phosphonates, thereby decreasing the therapeutic dosage over time, while at the same time preserving joint integrity. Said methods of treatment comprise one or more sixty (60)-day treatment periods, comprised of an optional NSAID administration regimen and a phosphonate administration regimen, wherein (a) said optional NSAID administration regimen comprises the administration to said subject of NSAID at a level of from 20% to 80%, preferably from 20% to 70%, most preferably from 20% to 50%, of the conventionally prescribed daily dose on each day that said NSAID is administered; provided that said NSAID is administered in sufficient quantities and on a sufficient number of days to alleviate symptoms of inflammation, and wherein (b) said phosphonate administration regimen comprises the administration to said subject of a phosphonate at a dose equivalent to a systemic level of from about 0.0005 mgP/kg to about 1.0 mgP/kg per day that said phosphonate is administered; provided that said phosphonate is administered at least 1 day of every said sixty (60)-day treatment period.

DEFINITIONS AND USAGE OF TERMS

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 8 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Carbocyclic ring" or "Carbocycle" as used herein is an unsubstituted or substituted, saturated, unsaturated or aromatic, hydrocarbon ring, generally containing from 3 to 8 atoms, preferably from 5 to 7, atoms. Carbocyclic rings may be monocyclic, having from 3 to 8, preferably from 5 to 7, carbon atoms, or they may be polycyclic. Polycyclic carbocycles consisting of two rings generally have from 6 to 16, preferably from 10 to 12, atoms. Polycyclic carbocycles consisting of three rings generally contain from 13 to 17, preferably from 14 to 15, atoms.

"Heterocyclic ring" or "heterocycle" as used herein is an unsubstituted or substituted, saturated, unsaturated or aromatic ring comprised of 3 to 8, preferably 5–7 carbon atoms, and one or more additional heteroatoms in the ring. The term "heterocyclic ring moieties" as used herein encompasses monocyclic or polycyclic ring systems, fused or unfused, uusaturated, saturated or unsubstituted. Monocyclic heterocyclic ring moieties generally contain from 3 to 8 atoms, preferably from 5 to 7, atoms. Polycyclic heterocyclic ring moieties consisting of two rings generally contain from 6 to 16, preferably from 10 to 12, atoms. Polycyclic heterocyclic ring moieties consisting of three rings generally contain from 13 to 17 atoms, preferably from 14 to 15, atoms. In addition, a polycyclic heterocyclic ring moiety may consist solely of heterocycles (one of which must contain a nitrogen atom), or of both heterocycles (one of which must contain a nitrogen atom) and carbocycles. Each heterocyclic ring moiety must have at least one nitrogen atom. Unless otherwise stated, any additional heteroatom in the heterocyclic ring moiety may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl, hydroxypropyl, and hydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., alkyl-NH—) such as methyl amine.

"Alkylamino" is an amino moiety having one or two alkyl substituents (e.g., —N-alkyl), such as dimethylamine.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl—).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, (e.g., R—C(=O)—). Preferred alkylacyl groups include, but are not limited to, acetyl, propionyl, butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

In the phosphonate compounds described in Parts I.B. and I.C. herein, the term "thio-substituent" is depicted by $SR^6$ or $R^8SR^6$, wherein $R^8$ is a $C_1$–$C_8$ alkyl. Particular thio-substituents include thiol (—SH, where $R^6$=H); thioesters

(S—CR$^7$, where $R^6$ is COR$^7$); thiocarbamates

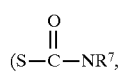
(S—C—NR$^7$, where $R^6$ is CONR$^7$); dithiocarbamates

(S—C—NR$^7$, where $R^6$ is CSNR$^7{}_2$); dithioesters

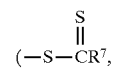
(—S—CR$^7$, where $R^6$ is CSR$^7$); thiocarbonates

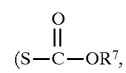
(S—C—OR$^7$, where $R^6$ is C(O)OR$^7$), and dithiocarbonates

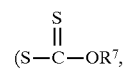
(S—C—OR$^7$, where $R^6$ is C(S)OR$^7$). $R^7$ as used herein is hydrogen or substituted or unsubstituted $C_1$–$C_8$ alkyl. It is to be understood that the $SR^6$ groups defined above can be preceded by an $R^8$ (i.e. a $C_1$–$C_8$ alkyl); this would yield alkyl thiols, alkyl thioesters, alkyl dithioesters, alkyl thiocarbamates, alkyl dithiocarbamates, alkyl thiocarbonates and alkyl dithiocarbonates.

The terms "bisphosphonate" or "bisphosphonic acid" as used herein relate to those phosphonate or phosphonic acids that have two phosphonate groups attached to the same carbon atom and are used interchangeably with the terms diphosphonate and diphosphonic acids. Using the structures of the phosphonate active ingredients described in Parts B and C herein, in these compounds the moiety R is $PO_3H_2$.

A "pharmaceutically-acceptable" salt is a catonic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred catonic salts include the alkali-metal salts (such as sodium and potassium), and alkaline earth metal salts (such as magnesium and calcium). Preferred anionic salts include the halide (such as chloride), acetates and phosphate salts.

A "biohydrolyzable ester" is an ester of thio-substituted phosphate compounds that does not interfere with the activity of the compounds, or that is readily metabolized by a human or other mammal to yield an active compound. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxymethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

The term "systemic level" as used herein relates to that dosage of the phosphonate compound in mgP/kg suitable for use in the methods of the present invention. The claimed phosphonate dosage level of 0.0005 mgP/kg to 1.0 mgP/kg is the dose to be used in the methods of treatment described herein when said dose is delivered systemically, i.e. parenterally. Oral administration is certainly contemplated for use herein, and for compliance and convenience considerations is preferred. Since adsorption of phosphonates administered orally is from 1% to 5%, the oral dosage level is from about twenty-fold to one-hundred fold, higher than the systemic dosage.

DESCRIPTION OF THE INVENTION

The present invention provides methods of treating a human or other animal subject afflicted with arthritis. Said methods inhibit intraarticular bone and joint destruction, substantially reduce or alleviate periarticular inflammation, and allow repair of subchondral bone in said subject. The phosphonate and NSAID active agents act in synergy with one another; i.e. the benefits exhibited when said active agents are used in the same therapeutic treatment regimen are greater than the sum of those benefits seen when either agent is administered alone. In addition, said method of treatment for arthritis utilizes significantly reduced dosages of the NSAID active agent, while at the same time preserving intraarticular bone and joint integrity, yet reducing the undesirable side effects associated with chronic NSAID therapy. In addition, said methods may allow a reduction in the dosage of the phosphonate compound administered over time. Said method comprises one or more sixty (60)-day treatment periods, comprised of an optional NSAID administration regimen and a phosphonate administration regimen, wherein (a) said optional NSAID administration regimen comprises the administration to said subject of NSAID at a level of from 20% to 80%, preferably from 20% to 70%, most preferably from 20% to 50%, of the conventionally prescribed daily dose on each day that said NSAID is administered; provided that said NSAID is administered in sufficient quantities and on a sufficient number of days to alleviate symptoms of inflammation, and wherein (b) said phosphonate administration regimen comprises the administration to said subject of a phosphonate at a dose equivalent to a systemic level of from about 0.0005 mgP/kg to about 1.0 mgP/kg per day that said phosphonate is administered; provided that said phosphonate is administered at least 1 day of every said sixty (60)-day treatment period.

The methods of treatment described herein are suitable for use as long-term maintenance therapies for use in treating patients with arthritis. Long term maintenance therapies generally preferably consist of sequential sixty (60)-day treatment periods, which would vary in dosages and/or types of NSAIDs and/or phosphonates, each treatment period following one after the other. As stated hereinabove, the methods of treatment described herein result in a reduction of inflammation of soft tissue in the periarticular area, but also inhibits the destruction of bone and hard tissue in the intraarticular area of the joint, thereby allowing repair of the subchondral bone.

The present methods allow a reduction in the amount of NSAIDs administered to an arthritis patient over time in two ways: 1) there is a reduction of from 20% to 80%, preferably from 30% to 80%, most preferably from 50% to 80%, of the conventional therapeutic dosages prescribed to patients per day in the active disease state; and 2) there may be a reduction in the amount NSAID administered over time via a reduction in the amount of days during which NSAID is administered to the arthritic patient. The term "conventional therapeutic dosage" as used herein relates to the daily dose of the particular NSAID as listed in the 46th Edition of the *Physician's Desk Reference* (1992). When several dosage levels are mentioned, the conventional therapeutic dose for the particular NSAID is that dose listed for active stages of the disease or for relief of pain. Occasionally, there is a higher dose listed to be used in limited periods (e.g. during active flares) that is considerably higher (often 1½ to 2 times higher) than the conventional therapeutic dose. The term "active flare period" as used herein relates to that period or phase of arthritis characterized by a sudden exacerbation of the disease, generally elicited as a rapid swelling of the soft tissue and increases in pain, stiffness, and inflammation. Accordingly, the reduction in the amount of NSAID administered over time results from both a lowering of the daily dose, and a reduction in the number of days the patient is dosed. It is generally believed that most intraarticular damage to the bone and hard tissues occurs during active flare periods.

The methods of the present invention allow a significant reduction in the conventional therapeutic daily dosage of NSAIDs; the ultimate aim of the present therapy would be to withdraw the administration of NSAID entirely and administer only a phosphonate compound. Since the therapeutic treatment periods described herein may achieve the administration of NSAID on a fewer number of days during the treatment period and reduces the daily dosage of NSAID, there will be a reduction in the total amount of NSAID administered over time. In addition to significantly alleviating the many undesirable side effects associated with chronic NSAID therapy, the present method of treatment inhibits the destruction of bone and hard tissue in the intraarticular area of the afflicted joints, allowing repair of the subchondral bone. Over time, in many patients, this results in fewer flare periods and, as a result, less bone and joint destruction and less inflammation and pain.

The particular regimens to be followed in the treatment periods described herein may be varied from patient to patient, depending on the particular characteristics exhibited in the patient at any given time. Accordingly, the sixty (60)-day treatment periods can be varied, one after the other, taking into account the condition and needs of the patient. The ultimate aim of this therapy is to continually reduce the dosage needed of NSAIDs (both the daily dosage and the number of days dosing is needed) while at the same time maintaining or reducing the incidence of active flare periods, and controlling the frequency and severity of inflammation. Various, more specific treatment regimens are described hereinafter.

ACTIVE MATERIALS

I. Bone-Active Phosphonates:

The methods of this invention involve the administration of a certain bone-active phosphonates, specifically the compound risedronate, as well as quarternary-nitrogen containing phosphonate compounds, and sulfur-containing (e.g. thio-substituted) phosphonates, as will be described hereunder.

A. The Risedronate Active Ingredient

The term "risedronate", as used herein, denotes the diphosphonate compound 3-pyridyl-1-hydroxyethylidene-1, 1-bisphosphonic acid and has the following structure:

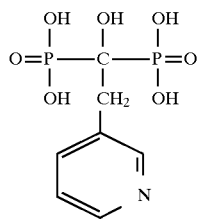

The compound risedronate is further described in the following publications, all hereby incorporated by reference herein: EPO Patent Application 0,186,405 of Benedict et al., (assigned to The Procter & Gamble Co.), published Jul. 2, 1986; and "An International Conference, Bisphosphonates: Current Status and Future Prospects, The Royal College of Physicians, London, England, May 21–22, 1990, organized by IBC Technical Services.

The term "risedronate active ingredient" includes risedronate, risedronate salts, and risedronate esters, or any mixture thereof. Any pharmaceutically-acceptable, non-toxic salt or ester of risedronate may be used as the risedronate active ingredient in the novel oral dosage forms of the present invention. The salts of risedronate may be acid addition salts, in particular the ammonium and hydrochloride, but any pharmaceutically-acceptable, non-toxic organic or inorganic acid salt may be used. In addition, salts formed with the carboxylic acid group may be used, including, but not limited to, alkali metal salts (K, Na) and alkaline earth metal salts (Ca, Mg), the Ca- and Na-salts being preferred.

Particularly, other esters of risedronate which are suitable for use as the active ingredient in the invention disclosed herein are straight chain or branched chain $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl esters, including, but not limited to, vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl esters, including, but not limited to, phenyl, toluyl, xylyl, and naphthyl; alicyclic esters, including, but not limited to, menthyl; and aralkyl esters, including, but not limited to, benzyl, and phenethyl.

B. Quarternary Nitrogen-Containing Phosphonate Active Ingredients

In addition, phosphonate compounds suitable for use herein are those quaternary nitrogen-containing heterocyclic phosphonate compounds, and their pharmaceutically-acceptable salts and esters, having the following structure:

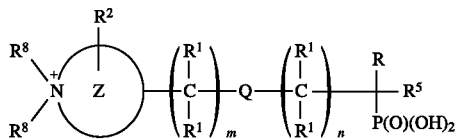

wherein m and n are integers from 0 to 10; m+n is from 0 to 10;

(a) Q is a covalent bond or a moiety selected from O, S, $NR^1$;

(b) Z is a saturated, unsaturated, or aromatic, monocyclic or polycyclic heterocycle containing one or more heteroatoms selected from O, S, or N, wherein at least one heteroatom is a quaternary nitrogen atom;

(c) R is COOH; $PO_3H_2$; $SO_3H$; or $P(O)(OH)R_4$, wherein $R_4$ is substituted or unsubstituted alkyl of 1–8 carbon atoms;

(d) each $R_1$ is selected from the group consisting of nil; $SR^6$; $R^9SR^6$; hydrogen; hydroxy; substituted or unsubstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; —$C(O)R^3$; arylalkyl; nitro; substituted or unsubstituted aryl, and combinations thereof.

(e) each $R_2$ is one or more substituents on the Z moiety independently selected from the group consisting of $SR^6$; $R^9SR^6$; hydrogen; substituted or unsubstituted $C_1$–$C_8$ alkyl; —$OR^3$; —$CO_2R^3$; —$O_2CR^3$; —$NR^3{}_2$; —$N(R^3)C(O)R^3$; —$C(O)N(R^3)_2$; halogen; hydroxy; —$C(O)R^3$; arylalkyl; nitro; substituted or unsubstituted aryl;

(f) each $R_3$ is independently selected from the group consisting of hydrogen, substituted or unsubstituted alkyl having from 1–8 carbon atoms, and $R^9SR^6$;

(g) $R_5$ is selected from the group consisting of hydrogen; halogen; $SR^6$; $R^9SR^6$; amino; hydroxy; and substituted or unsubstituted $C_1$–$C_8$ alkyl;

(h) each $R^6$ is independently selected from the group consisting of H; —$C(O)R^7$; —$C(S)R^7$; —$C(O)NR^7{}_2$; —$C(S)N(R^7)_2$; —$C(S)OR^7$; —$C(O)OR^7$; wherein $R^7$ is hydrogen or substituted or unsubstituted $C_1$–$C_8$ alkyl.

(i) each $R^8$ is independently selected from the group consisting of nil, substituted or unsubstituted alkyl having 1–35 carbon atoms, substituted or unsubstituted phenyl, benzyl, or $R^9SR^6$; and (j) $R^9$ is a substituted or unsubstituted $C_1$–$C_8$ alkyl;

The preferred diphosphonopyridinium compounds for use in the methods of the present invention may have the following general structure:

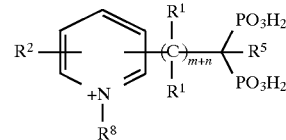

Also preferred for use in the methods described herein are diphosphonopyridinium compounds wherein the linking chain has a heteroatom, i.e., Q=S, O, or $NR^1$.

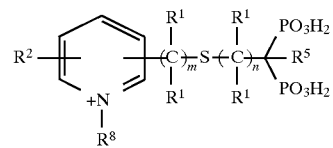

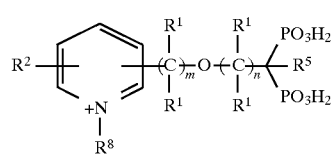

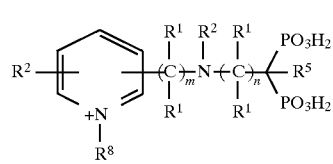

Preferred compounds for use in the methods of the present invention wherein Z is a polycyclic heterocycle include those compounds having the following structure:

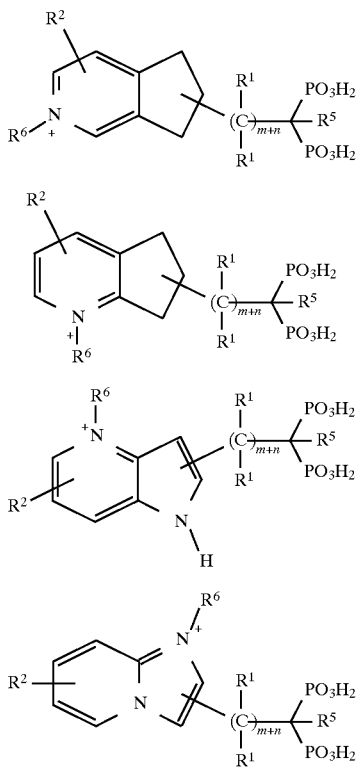

Compounds of the present invention may also have the following general structure:

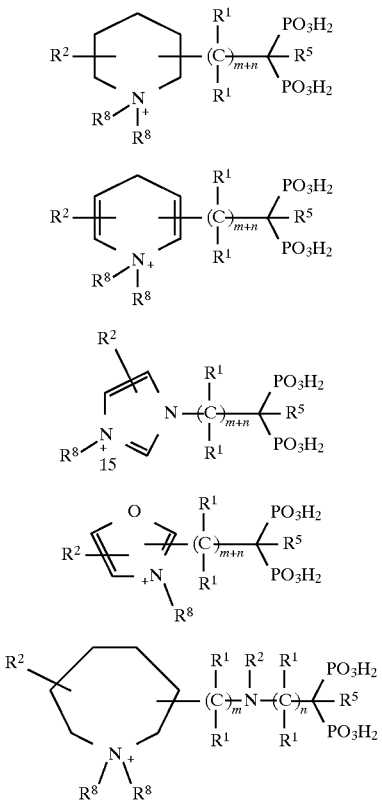

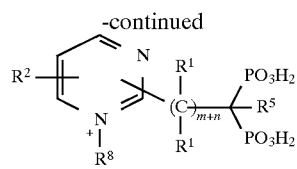

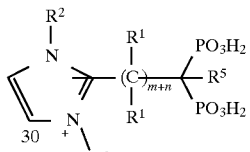

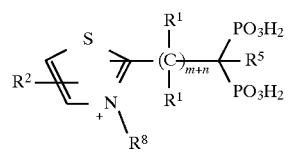

These compounds are described in greater detail in U.S. Ser. No. 07/890,885, to Ebetino, et al., filed May 29, 1992, hereby incorporated by reference herein.

Other suitable quaternary nitrogen-containing phosphonate compounds suitable for use in the methods described herein are those bicyclic ring-containing phosphonates, and their pharmaceutically-acceptable salts and esters, having the following general structure:

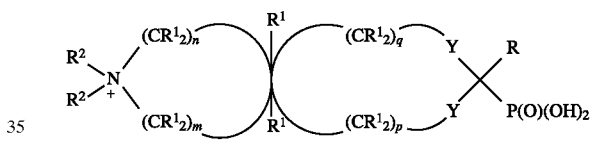

wherein (a) Y is independently selected from nil, O, S, $NR^1$;

(b) m and n and ii+n are integers from 0 to 5; p and q and p+q are integers from 0 to 3;

(c) each $R^1$ is independently selected from the group consisting of nil, $R^9SR^6$, $SR^6$, hydrogen, hydroxy; unsubstituted or substituted $C_1$–$C_8$ alkyl, —$OR^3$, —$CO_2R^3$, —$O_2CR^3$, $NR^3{}_2$, —$N(R^3)C(O)R^3$, —$C(O)N(R^3)_2$, halogen, —$C(O)R^3$ arylalkyl, nitro, unsubstituted or substituted aryl, and combinations thereof;

(d) each $R^2$ is selected from the group consisting of a substituted or unsubstituted $C_1$–$C_{35}$ alkyl, substituted or unsubstituted phenyl, benzyl, or $R^9SR^6$;

(e) each $R^3$ is independently selected from the group consisting of hydrogen, substituted or unsubstituted $C_1$–$C_8$ alkyl, and $R^9SR^6$.

(f) each $R^6$ is independently selected from the group consisting of H, —$C(O)R^7$, $C(O)OR^7$, $C(S)OR^7$, $C(S)R^7$, $C(O)NR^7{}_2$; $C(S)NR^7{}_2$, wherein $R^7$ is hydrogen, or substituted or unsubstituted $C_1$–$C_8$ alkyl;

(g) R is COOH, $SO_3H_2$, $PO_3H_2$, or $P(O)(OH)R_4$, wherein $R_4$ is substituted or unsubstituted $C_1$–$C_8$ alkyl; and (h) $R^9$ is substituted or unsubstituted $C_1$–$C_8$ alkyl.

Especially preferred bicyclic compounds for use in the method of treatment described herein are substituted or unsubstituted octahydro diphosphonopyrindinium, and the pharmaceutically-acceptable salts and esters thereof, having the general structures:

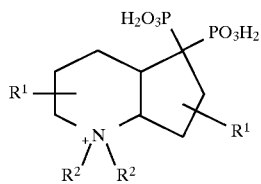

referred to herein as "unsubstituted or substituted octahydro-5,5-diphosphono-1,1-dialkyl-1-pyrindinium";

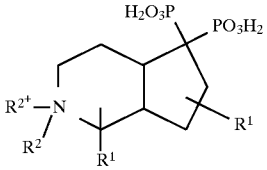

referred to herein as "unsubstituted or substituted octahydro-5,5-diphosphono-2,2-dialkyl-2-pyrindinium salts";

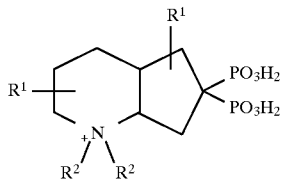

referred to herein as "unsubstituted or substituted octahydro-6,6-diphosphono-1,1-dialkyl-1-pyrindinium salts";

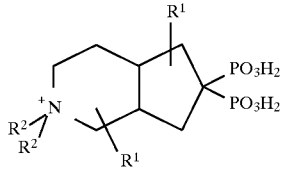

referred to herein as "unsubstituted or substituted octahydro-6,6-diphosphono-2,2-dialkyl-2-pyrindinium salts";

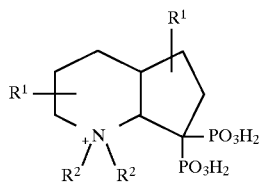

referred to herein as "octahydro-7,7-diphosphono-1,1-dialkyl-1-pyrindinium salts";

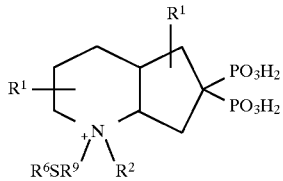

referred to herein as "octahydro-6,6-diphosphono-1-alkyl-1-thioalkyl-1-pyrindinium salts";

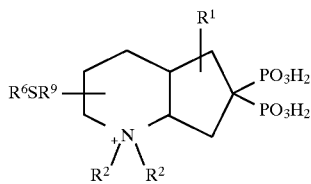

referred to herein as thio-substituted "octahydro-6,6-diphosphono-1,1-dialkyl-1-pyrindinium salts"; and

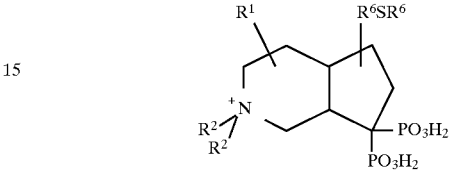

referred to herein as "a thio-substituted octahydro-7,7-diphosphono-2,2-dialkyl-2-pyrindinium salts".

These compounds are described in greater detail in U.S. Ser. No. 07/891,487 to Ebetino, et al., filed May 29, 1992, hereby incorporated by reference herein.

Also suitable phosphonate compounds for use in the methods described herein are those quaternary nitrogen-containing phosphonate compounds, and the pharmaceutically-acceptable salts and esters thereof, having the following general structure:

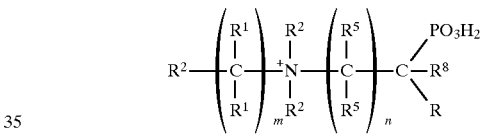

wherein m is an integer from 0–10; n is an integer from 1–10; and m+n is from 1–10;

(a) $R^1$ is selected from the group consisting of nil; —$SR^6$; —$R^9SR^6$; hydrogen; substituted or unsubstituted $C_1$–$C_8$ alkyl; —$OR^3$; —$CO_2R^3$; —$O_2CR^3$; —$NR^3_2$; —$N(R^3)C(O)R^3$; —$C(O)N(R^3)_2$; halogen; —$C(O)R^3$; nitro; hydroxy; substituted or unsubstituted saturated monocyclic or polycyclic heterocyclic rings; substituted or unsubstituted saturated monocyclic or polycyclic carbocyclic rings;

(b) $R^5$ is selected from the group consisting of —$SR^6$; —$R^9SR^6$; hydrogen; substituted or unsubstituted $C_1$–$C_8$ alkyl; —$OR^3$; —$CO_2R^3$; —$O_2CR^3$; —$NR^3_2$; —$N(R^3)C(O)R^3$; —$C(O)N(R^3)_2$; halogen; —$C(O)R^3$; nitro; hydroxy; substituted or unsubstituted saturated monocyclic or polycyclic heterocyclic rings; substituted or unsubstituted saturated monocyclic or polycyclic carbocyclic rings; substituted or unsubstituted unsaturated monocyclic or polycyclic heterocyclic rings; substituted or unsubstituted unsaturated monocyclic or polycyclic carbocyclic rings and combinations thereof;

(c) each $R^2$ is selected from the group consisting of substituted or unsubstituted $C_1$–$C_{35}$ alkyl; unsubstituted or substituted phenyl; benzyl; or $R^9SR^6$;

(d) $R^3$ is selected from the group consisting of H; unsubstituted or substituted $C_1$–$C_8$ alkyl; $R^9SR^6$;

(e) $R^6$ is selected from the group consisting of —H; —$C(O)R^7$; —$C(S)R^7$; —$C(O)N(R^7)_2$; —$C(O)OR^7$; —$C(S)N(R^7)_2$; —$C(S)OR^7$; where $R^7$ is hydrogen or unsubstituted or substituted $C_1$–$C_8$ alkyl;

(f) R is selected from the group consisting of —COOH; —SO$_3$H; –PO$_3$H$_2$; and -P(O)(OH)R$^4$, where R$^4$ is an alkyl group having 1–3 carbons.

(g) R$^9$ is substituted or unsubstituted C$_1$–C$_8$ alkyl;

(h) R$^8$ is selected from the group consisting of hydrogen, halogen; SR$^6$; R$^9$SR$^6$; amino; hydroxy; substituted and unsubstituted C$_1$–C$_8$ alkyl;

Preferred quaternary nitrogen-containing phosphonates having an R$^1$ moiety selected from the R$^1$ moieties described herein before include,

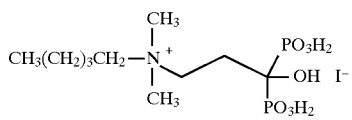

N-(3-hydroxy-3,3-diphosphonopropyl)-N,N-dimethyl-N-pentylammonium chloride

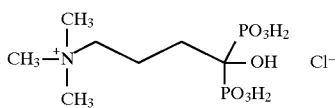

N-(4-hydroxy-4,4-diphosphonobutyl)-N,N,N-trialkylammonium salt

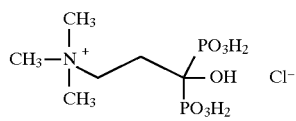

N-(3-hydroxy-3,3-diphosphonopropyl)-N,N,N-trialkylammonium salts.

Preferred quaternary nitrogen-containing phosphonates having a saturated monocyclic or polycyclic heterocycle as an R$^1$ moiety wherein the quaternary nitrogen atom is linked via a linking chain to the phosphonic acid carbon include:

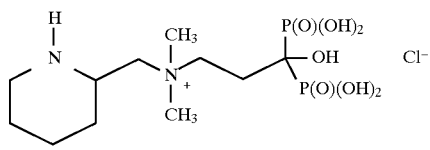

N-(3-hydroxy-3,3-diphosphonopropyl)-N,N-dimethyl-N-(2-piperidinemethyl) ammonium chloride.

Additionally, preferred compounds for use in the methods of the present invention include those compounds having the following structures:

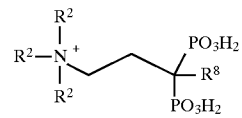

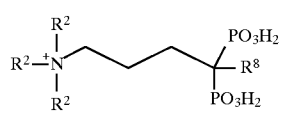

Preferred compounds for use in the methods of the present invention also include the thio-substituted quaternary nitrogen containing phosphonates.

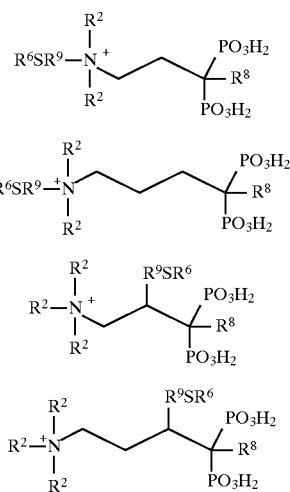

These compounds are described in greater detail in U.S. Ser. No. 07/891,355 to Francis, et al., filed May 29, 1992, hereby incorporated by reference herein.

C. Sulfur-Containing Phosphonate Active Ingredients

Sulfur-containing (e.g., thio-substituted) phosphonate compounds are also suitable phosphonate active ingredients for use in the treatment regimens described herein. Especially suitable are those thio-substituted nitrogen-containing heterocyclic phosphonate compounds having the following general structure:

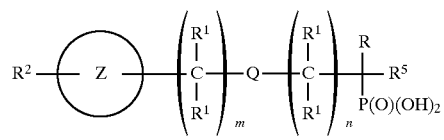

(a) Z is a monocyclic or polycyclic heterocyclic ring moiety containing one or more heteroatoms selected from O, S, or N, at least one of which is N;

(b) Q is covalent bond; O, S, N, or NR$^1$;

(c) R is COOH, SO$_3$H, PO$_3$H$_2$, or P(O)(OH)R$^4$, wherein R$^4$ is substituted or unsubstituted C$_1$–C$_8$ alkyl;

(d) each R$^1$ is independently selected from —SR$^6$; —R$^8$SR$^6$; nil; hydrogen; unsubstituted or substituted C$_1$–C$_8$ alkyl; unsubstituted or substituted aryl; hydroxy; —CO$_2$R$^3$; —O$_2$CR$^3$; —NR$^3{}_2$; —OR$^3$; —C(O)N(R$^3$)$_2$; —N(R$^3$)C(O)R$^3$; substituted or unsubstituted benzyl; nitro; or combinations thereof;

(e) R$^2$ is one or more substituents on atoms in the Z moiety and is independently selected from —SR$^6$ and —R$^8$SR$^6$; where R$^6$ is H; —CO$_2$R$^3$; —O$_2$CR$^3$; —NR$^3{}_2$; —N(R)$^3$C(O)R$^3$; and nil; hydrogen; unsubstituted or substituted C$_1$–C$_8$ alkyl; unsubstituted or substituted aryl; hydroxy; substituted or unsubstituted benzyl; nitro; or combinations thereof;

(f) each R$^3$ is independently selected from hydrogen; substituted or unsubstituted C$_1$–C$_8$ alkyl; or R$^8$SR$^6$;

(g) R$^5$ is selected from —SR$^6$, R$^8$SR$^6$, hydrogen; hydroxy; amino; halogen; unsubstituted or substituted C$_1$–C$_8$ alkyl; and (h) R$^6$ is independently selected from H; —C(O)R$^7$; C(S)R$^7$; C(O)NR$^7{}_2$; C(S)NR$^7{}_2$; C(O)(OR$^7$); and C(S)(OR$^7$); wherein R$^7$ is hydrogen; or unsubstituted or substituted C$_1$–C$_8$ alkyl;

(i) $R^8$ is a substituted or unsubstituted $C_1$–$C_8$ alkyl; and at least one of $R^1$, $R^2$, $R^3$ or $R^5$ must be $SR^6$ or $R^8SR^6$.

As stated above, it is essential that at least one of $R^1$, $R^2$, $R^3$ and $R^5$ is $SR^6$ or $R^8SR^6$; when any of $R^1$, $R^2$, $R^3$, or $R^5$ is $SR^6$ or $R^8SR^6$, the heterocyclic phosphonate is thio-substituted. Suitable thio-substituents in the following compounds preferred for use herein are thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonates.

The preferred thio-substituted, pyridine-containing bisphosphonic acid compounds useful as phosphonate active agents in the methods of the present invention may have the following general structures:

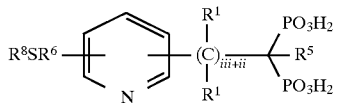

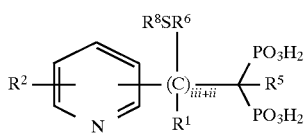

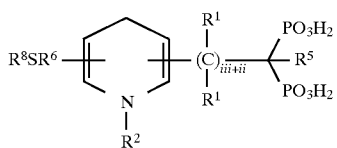

Also preferred are thio-substituted, pyridine-containing bisphosphonates wherein the linking chain has a heteroatom, i.e. Q=S, O, N, or $NR^1$.

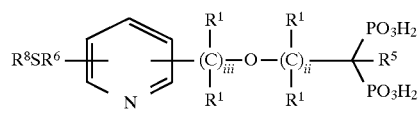

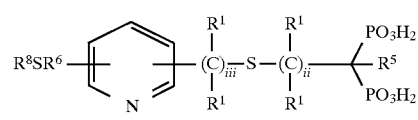

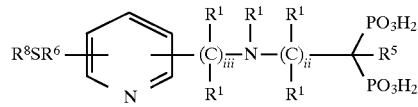

In addition, the thio-substituted piperidine bisphosphonic acids, and the pharmaceutically-acceptable salts and esters thereof, suitable for use in the methods of the present invention may alternatively have the following general structures:

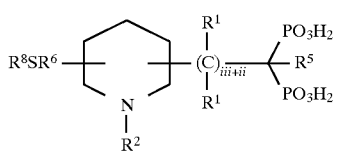

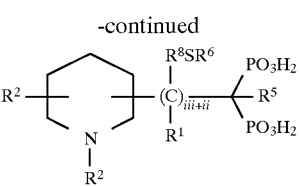

Other thio-substituted bisphosphonic acid compounds include those compounds wherein the Z moiety is a polycyclic heterocyclic ring moiety consisting of two rings.

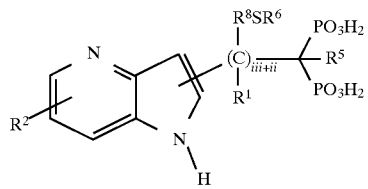

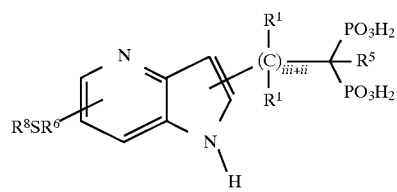

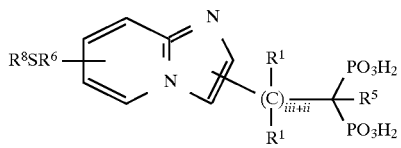

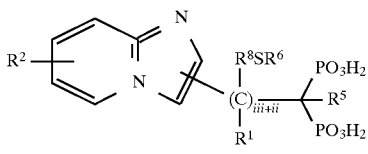

Other preferred thio-containing heterocycle substituted bisphosphonic acids, are those compounds where the Z moiety is a pyrimidine. These compounds, and the pharmaceutically acceptable salts and esters thereof, have the general structures:

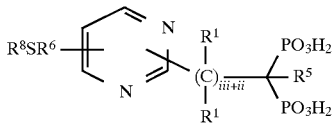

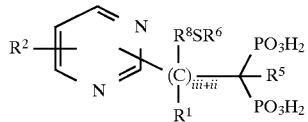

Other suitable thio-substituted heterocyclic bisphosphonic acids include those compounds wherein Z is a seven-membered nitrogen-containing heterocycle, having the following general structure:

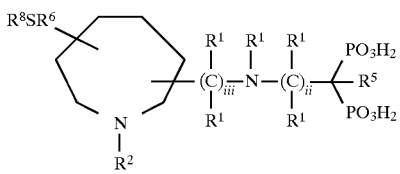

Thio-substituted heterocyclic bisphosphonic acids wherein the Z moiety is a five-membered heterocycle are also preferred phosphonate active ingredients and may have the following general structure:

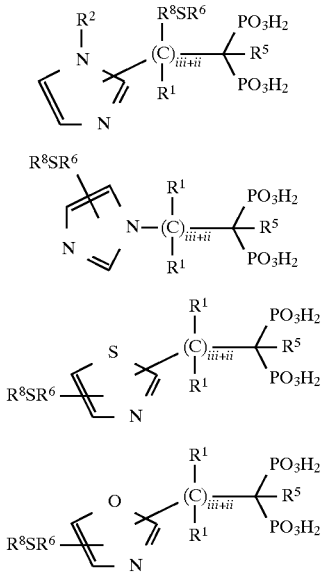

These compounds are described in greater detail in U.S. Ser. No. 07/891,490 to Kaas, et al., filed May 29, 1992, hereby incorporated by reference herein.

Other suitable for use herein as phosphonate compounds are those thio-substituted bicyclic compounds having the following general structure:

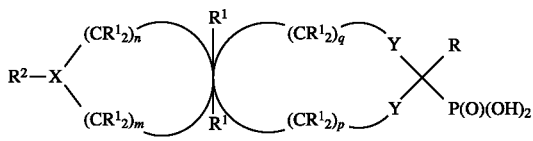

wherein (a) X and Y are independently selected from nil, O, S, and N;

(b) R is COOH, SO3H, $PO_3H_2$, $P(O)(OH)R^4$, wherein $R^4$ is substituted or unsubstituted $C_1$–$C_8$ alkyl;

(c) m and n are integers from 0 to 5, and m+n equals 0 to 5;

(d) p and q are integers from 0 to 3, and p+q equals 0 to 3;

(e) each $R^1$ is independently selected from —$SR^6$; $R^8SR^6$; nil; hydrogen; unsubstituted or substituted $C_1$–$C_8$ alkyl; unsubstituted or substituted aryl; hydroxy; —$CO_2R^3$; —$O_2CR^3$; —$NR^3{}_2$; —$OR^3$; —$C(O)N(R^3)_2$; —$N(R^3)C(O)R^3$; substituted or unsubstituted benzyl; nitro; and combinations thereof;

(f) $R^2$ is one or more substituents of X and Y and is independently selected from the group consisting of $R^8SR^6$; nil; hydrogen; unsubstituted or substituted $C_1$–$C_8$ alkyl; unsubstituted or substituted aryl; —$CO_2R^3$; —$C(O)N(R^3)_2$; substituted or unsubstituted benzyl; or combinations thereof;

(g) $R^3$ is independently selected from hydrogen; substituted or unsubstituted $C_1$–$C_8$ alkyl; or $R^8SR^6$;

(h) $R^6$ is independently selected from H; $C(O)R^7$; —$C(S)R^7$; $C(O)N(R^7)_2$; $C(S)N(R^7)_2$, $C(O)OR^7$; and $C(S)OR^7$; wherein $R^7$ is hydrogen, or substituted or unsubstituted $C_1$–$C_8$ alkyl; and (i) $R^8$ is substituted or unsubstituted $C_1$–$C_8$ alkyl; provided that at least one of $R^1$, $R^2$, and $R^3$ is $SR^6$ or $R^8SR^6$.

Preferred compounds for use in the methods of the present invention are thio-substituted octahydro pyrindine diphosphonic acids, and the pharmaceutically-acceptable salts and esters thereof, having the general structures:

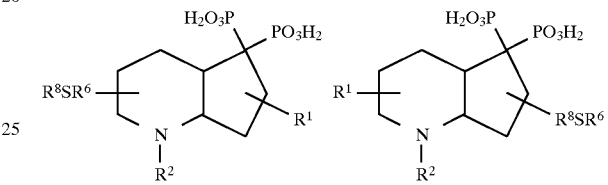

referred to herein as "thio-substituted octahydro-1-pyrindine-5,5-diphosphonic acids";

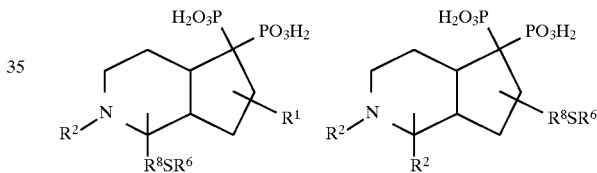

referred to herein as "thio-substituted octahydro-2-pyrindine-5,5-diphosphonic acids";

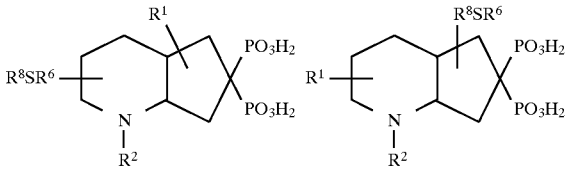

referred to herein as "thio-substituted octahydro-1-pyrindine-6,6-diphosphonic acids";

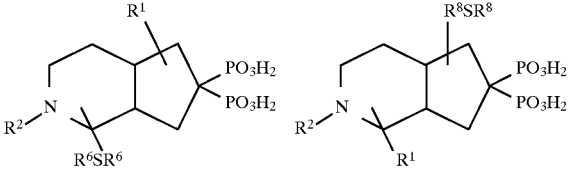

referred to herein as "thio-substituted octahydro-2-pyrindine-6,6-diphosphonic acids";

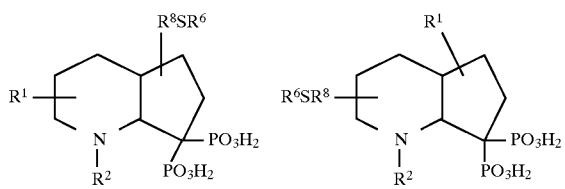

referred to herein as "thio-substituted octahydro-1-pyrindine-7,7-diphosphonic acids"; and

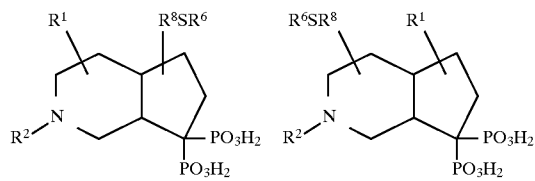

referred to herein as "thio-substituted octahydro-2-pyrindine-7,7-diphosphonic acids"; and

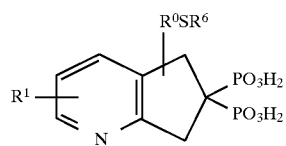

referred to herein as "dihydro-1-pyrindine-6,6-diphosphonic acid"; and

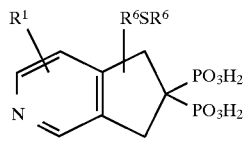

referred to herein as "dihydro-2-pyrindine-6,6-diphosphonic acid".

These and other compounds are described in greater detail in U.S. Ser. No. 07/890,886 to Kaas, et al., filed May 29, 1992, hereby incorporated by reference herein.

Other preferred phosphonate compounds for use in the methods described herein are those sulfur-containing phosphonate compounds having the following general structure:

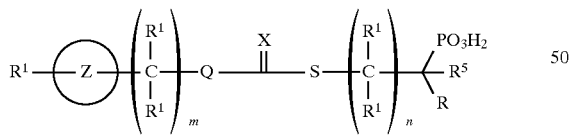

wherein m and n are integers 0 to 10 and m+n equals 0 to 10, and wherein (a) X is O or S;
(b) Z is a covalent bond; a monocyclic or polycyclic carbocyclic ring moiety; or a monocyclic or polycyclic heterocyclic ring moiety containing one or more heteroatoms selected from O, S, or N;
(c) Q is covalent bond; O; or S;
(d) R is COOH, $SO_3H$, $PO_3H_2$, or $P(O)(OH)R^4$, wherein $R^4$ is substituted or unsubstituted $C_1$–$C_8$ alkyl;
(e) each $R^1$ is independently selected from —$SR^6$; —$R^8SR^6$; nil; hydrogen; unsubstituted or substituted $C_1$–$C_8$ alkyl; monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy; —$CO_2R^3$; —$O_2CR^3$; —$NR^3_2$; —$OR^3$; —$C(O)N(R^3)_2$; —$N(R^3)C(O)R^3$; substituted or unsubstituted benzyl; nitro; or combinations thereof;

(f) $R^2$ is independently selected from —$SR^6$, —$R^8SR^6$, —$CO_2R^3$; —$O_2CR^3$; —$C(O)N(R^3)_2$; —$N(R)^3C(O)R^3$; and nil; hydrogen; unsubstituted or substituted $C_1$–$C_8$ alkyl; unsubstituted or substituted aryl; hydroxy; substituted or unsubstituted benzyl; nitro; or combinations thereof;

(g) each $R^3$ is independently selected from hydrogen; substituted or unsubstituted $C_1$–$C_8$ alkyl; or $R^8SR^6$;

(h) $R^5$ is selected from —$SR^6$, $R^8SR^6$, hydrogen; hydroxy; amino; halogen; unsubstituted or substituted $C_1$–$C_8$ alkyl;

(i) $R^6$ is independently selected from H; —$C(O)R^7$; and $C(O)NR^7_2$; wherein $R^7$ is hydrogen; or unsubstituted or substituted $C_1$–$C_8$ alkyl; and (j) $R^8$ is a substituted or unsubstituted $C_1$–$C_8$ alkyl.

Other thio-substituted compounds suitable for use herein have the following general structure:

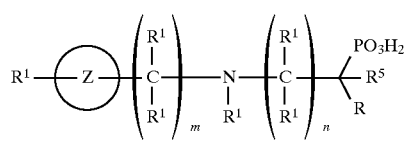

wherein m and n are integers from 0 to 10 and m+n equals 0 to 10 and wherein (a) Z is a covalent bond; a monocyclic or polycyclic carbocyclic ring moiety; or a monocyclic or polycyclic heterocyclic ring moiety containing one or more heteroatoms selected from O, S, or N;

(b) R is COOH; $SO_3H$; $PO_3H_2$ or $P(O)(OH)R^4$; wherein $R^4$ is $C_1$–$C_8$ alkyl;

(c) each $R^1$ is independently selected from —$SR^6$; —$R^8SR^6$; nil; hydrogen; unsubstituted or substituted $C_1$–$C_8$ alkyl; a monocyclic or polycyclic carbocyclic ring moiety; unsubstituted or substituted aryl; substituted or unsubstituted thiophene; substituted or unsubstituted oxathiazole; substituted or unsubstituted pyranones; substituted or unsubstituted furans; hydroxy; —$CO_2R^3$; —$O_2CR^3$; —$NR^3_2$; —$N(R^3)C(O)R^3$; —$OR^3$; —$C(O)N(R^3)_2$; substituted or unsubstituted benzyl; nitro; or combinations thereof;

(d) $R^2$ is independently selected from —$SR^6$; —$R^8SR^6$; —$CO_2R^3$; —$O_2CR^3$; —$NR^3_2$; —$N(R)^3C(O)R^3$; $OR^3$; —$C(O)N(R^3)_2$; nil; hydrogen; unsubstituted or substituted $C_1$–$C_8$ alkyl; unsubstituted or substituted aryl; hydroxy; substituted or unsubstituted benzyl; nitro; or combinations thereof;

(e) each $R^3$ is independently selected from hydrogen; substituted or unsubstituted $C_1$–$C_8$ alkyl; or $R^8SR^6$;

(f) $R^5$ is selected from —$SR^6$; $R^8SR^6$; hydrogen; hydroxy; unsubstituted or substituted $C_1$–$C_8$ alkyl; amino; halogen;

(g) $R^6$ is H; —$C(O)R^7$; —$C(S)R^7$; —$C(O)NR^7_2$; —$C(S)NR^7_2$; $C(O)OR^7$; or $C(S)OR^7$, wherein $R^7$ is hydrogen, or unsubstituted or substituted $C_1$–$C_8$ alkyl; and (i) $R^8$ is $C_1$–$C_8$ substituted or unsubstituted alkyl; and at least one of $R^1$, $R^2$, $R^3$ or $R^5$ is $SR^6$ or $R^8SR^6$.

Other thio-substituted phosphonate compounds have the following structure:

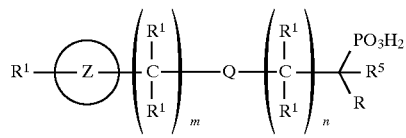

wherein m and n are integers from 0 to 10 and m+n equals 0 to 10, and wherein (a) Z is a covalent bond; a monocyclic or polycyclic carbocyclic ring moiety; or a monocyclic or polycyclic heterocyclic ring moiety containing one or more heteroatoms selected from O, S, or N;

(b) Q is covalent bond, S, O, N, or $NR^1$;

(c) R is COOH; $SO_3H$; $PO_3H_2$ or $P(O)(OH)R^4$; wherein $R^4$ is $C_1$–$C_8$ alkyl;

(d) each $R^1$ is independently selected from —$SR^6$; —$R^8SR^6$; nil; hydrogen; unsubstituted or substituted $C_1$–$C_8$ alkyl; substituted or unsubstituted monocyclic or polycyclic carbocycle; unsubstituted or substituted aryl; substituted or unsubstituted thiophene; substituted or unsubstituted oxathiazole; substituted or unsubstituted pyranone; substituted or unsubstituted furan; hydroxy; alkoxy; —$CO_2R^3$; —$O_2CR^3$; —$NR^3{}_2$; —$N(R^3)C(O)R^3$; —$OR^3$; —$C(O)N(R^3)_2$; substituted or unsubstituted benzyl; nitro; or combinations thereof;

(e) $R^1$ is one or more substituents selected from —$SR^6$; —$R^8SR^6$; —$CO_2R^3$; —$O_2CR^3$; —$C(O)N(R^3)_2$; —$NR^3{}_2$; —$N(R^3)C(O)R^3$; and nil; hydrogen; substituted or unsubstituted $C_1$–$C_8$ alkyl; substituted or unsubstituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or $R^8SR^6$;

(g) $R^5$ is selected from —$SR^6$; $R^8SR^6$; hydrogen; hydroxy; unsubstituted or substituted $C_1$–$C_8$ alkyl; amino; halogen;

(h) $R^6$ is H; —$C(O)R^7$; —$C(S)R^7$; —$C(O)NR^7{}_2$; —$C(S)NR^7{}_2$; $C(O)OR^7$; or $C(S)OR^7$, wherein $R^7$ is hydrogen, or unsubstituted or substituted $C_1$–$C_8$ alkyl; and (i) $R^8$ is $C_1$–$C_8$ substituted or unsubstituted alkyl; and at least one of $R^1$, $R^2$, $R^3$ or $R^5$ is $SR^6$ or $R^8SR^6$.

Preferred thioesters suitable for use in the methods described herein include compounds having the following general structures:

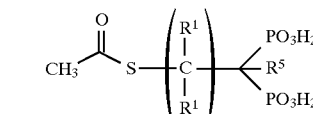

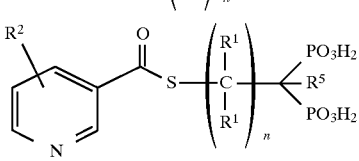

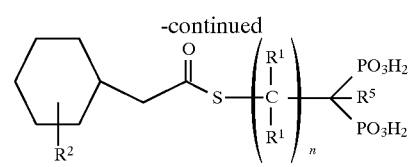

Preferred dithioesters include compounds having the following general structures:

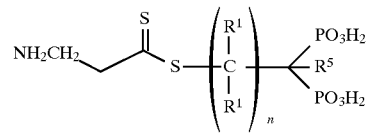

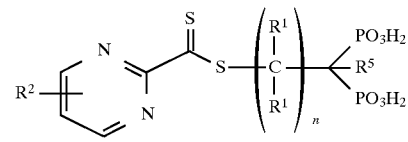

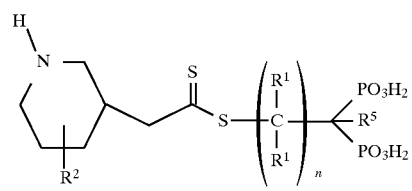

Preferred thiocarbonates include compounds which have the following general structures:

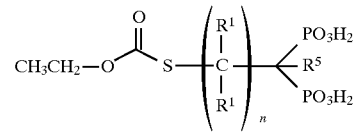

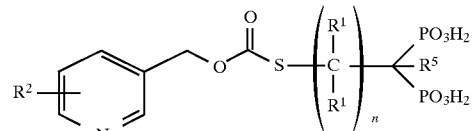

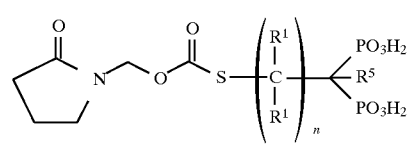

Preferred dithiocarbonates include compounds which have the following general structure:

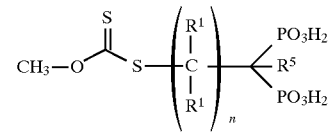

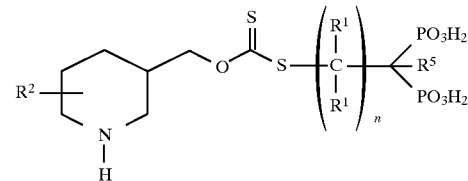

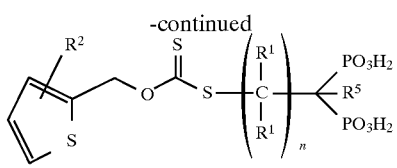

Preferred thio-substituted phosphonate compounds suitable for use in the treatment regimens of the present invention include, but are not limited to, compounds having the following general structures:

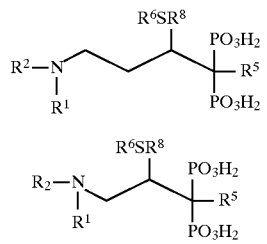

Especially preferred are the following thio-substituted aminoalkylidene bisphosphonate compounds:

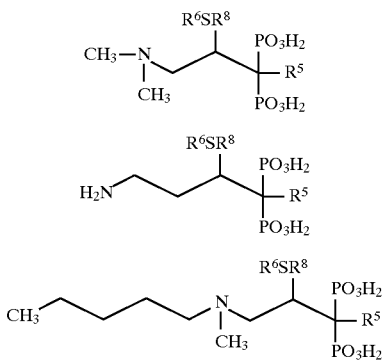

These compounds are described in greater detail in U.S. Ser. No. 07/891,309 to Francis, et al., filed May 29, 1992, hereby incorporated by reference herein.

SPECIFIC PHOSPHONATE ACTIVE INGREDIENTS

Specific phosphonate compounds which are suitable for use herein and are described in Parts I. A, B, and C hereinabove include, but are not limited to, the following compounds, and their pharmaceutically-acceptable salts and esters:

3-pyridyl-1-hydroxyethylidene-1,1-bisphosphinic acid;
N-(2'-(3'-methyl)-pyridinyl)aminomethane phosphonomethylphosphinic acid;
N-(2'-(5'-methyl)-pyridinyl)aminomethane phosphonomethylphosphinic acid;
N-(2'-(3'-methyl)-piperidinylidene)aminomethane phosphonomethylphosphinic acid;
N-(2'-(5'-methyl)-piperidinylidene)aminomethane phosphonomethylphosphinic acid;
2-(2'-pyridinyl)ethane-1-phosphono-1-methylphosphinic acid;
2-(2'-piperidinyl)ethane-1-phosphono-1-methylphosphinic acid;
2-(p-aminophenyl)-1-hydroxy-ethane-1-phosphono-1-methylphosphinic acid;
2-(m-aminophenyl)-1-hydroxy-ethane-1-phosphono-1-methylphosphinic acid;
N-(1-(5-amino-2-methyl-1-oxo)-pentyl)aminomethane phosphonomethylphosphinic acid;
N-(2'-(3'-methyl)-piperidinylidene)aminomethane phosphonobutylphosphinic acid;
S-(2'-pyridinyl)thiomethane phosphonomethylphosphinic acid;
2-(2-pyridyl)-1-hydroxyethane-1-phosphono-1-methylphosphinic acid;
2-(3-pyridyl)-1-hydroxyethane-1-phosphono-1-methylphosphinic acid;
2-(N-imidazoyl)-1-hydroxyethane-1-phosphono-1-methylphosphinic acid;
3-(N-pentyl-N-methylamino)-1-hydroxypropane-1-phosphono-1-methylphosphinic acid;
4-amino-1-hydroxybutane-1-phosphono-1-methylphosphinic acid;
3-(N-pyrollidino)-1-hydroxypropane-1-phosphono-1-methylphosphinic acid;
N-cycloheptyl aminomethanephosphonomethylphosphinic acid;
S-(p-chlorophenyl) thiomethanephosphonomethylphosphinic acid;
(7-dihydro-1-pyrindine) methanephosphonomethylphosphinic acid;
(7-dihydro-1-pyrindine) hydroxymethanephosphonomethylphosphinic acid;
(6-dihydro-2-pyrindine) hydroxymethanephosphonomethylphosphinic acid;
2-(6-pyrolopyrindine)-1-hydroxyethane-1-phosphono-1-methyl phosphinic acid;
1-aminoethane-1,1-bisphosphonic acid;
2-aminoethane-1,1-bisphosphonic acid;
3-aminopropane-1,1-bisphosphonic acid;
3-aminopropane-1-hydroxy-1,1-bisphosphonic acid;
3-(dimethylamino)-1-hydroxypropane-1,1-bisphosphonic acid;
3,3-dimethyl-3-amino-1-hydroxypropane-1,1-bisphosphonic acid;
phenylaminomethane bisphosphonic acid;
N,N-dimethylaminomethane bisphosphonic acid;
N-(2-hydroxyethyl)aminomethanebisphosphonic acid;
4-amino-1-hydroxybutane-1,1-bisphosphonic acid;
5-amino-1-hydroxypentane-1,1-bisphosphonic acid;
6-amino-1-hydroxyhexane-1,1-bisphosphonic acid;
indan-2,2-bisphosphonic acid;
hexahydroindan-2,2-bisphosphonic acid;
2-(2-pyridyl)-1-hydroxyethane-1,1-bisphosphonic acid;
N-(2-(5-amino)-pyridyl)-aminomethane bisphosphonic acid;
N-(2-(5-chloro)-pyridyl)-aminomethane bisphosphonic acid;
N-(2-(3-picolyl))-aminomethane bisphosphonic acid;
N-(2-(4-picolyl))-aminomethane bisphosphonic acid;
N-(2-(5-picolyl))-aminomethane bisphosphonic acid;
N-(2-(6-picolyl))-aminomethane bisphosphonic acid;
N-(2-(3,4-lutidine))-aminomethane bisphosphonic acid;
N-(2-pyrimidyl)-aminomethane bisphosphonic acid;
N-(2-pyridyl)-2-aminoethane-1,1-bisphosphonic acid;

2-(2-pyridyl)-ethane-1,1-bisphosphonic acid;
2-(3-pyridyl)-ethane-1,1-bisphosphonic acid;
2-(4-pyridyl)-ethane-1,1-bisphosphonic acid;
2-(2-(3-picolyl))-oxaethane-1,1-bisphosphonic acid;
2-(3-pyridyl)-1-hydroxyethane-1,1-bisphosphonic acid;
2-(N-imidazoyl)-1-hydroxyethane-1,1-bisphosphonic acid;
3-(N-pentyl-N-methylamino)-1-hydroxypropane-1,1-bisphosphonic acid;
3-(N-pyrollidino)-1-hydroxypropane-1,1-bisphosphonic acid;
N-cycloheptylaminomethane bisphosphonic acid;
S-(p-chlorophenyl) thiomethanebisphosphonic acid;
(7-dihydro-1-pyrindine)methanebisphosphonic acid;
(7-dihydro-1-pyrindine)hydroxymethanebisphosphonic acid;
(6-dihydro-2-pyrindine)hydroxymethanebisphosphonic acid;
2-(6-pyrolopyridine)-1-hydroxyethane-1,1-bisphosphonic acid;
3-amino-1-hydroxypropane-1,1-bisphosphonic acid;
6-amino-1-hydroxyhexane-1,1-bisphosphonic acid;
2-(3-pyridyl)-1-hydroxyethane-1,1-bisphosphonic acid;
2-(N-imidazoyl)-1-hydroxyethane-1,1-bisphosphonic acid;
3-(N-pentyl-N-methylamino)-1-hydroxypropane-1,1-bisphosphonic acid;
3-(N-pyrollidino)-1-hydroxypropane-1,1-bisphosphonic acid;
N-cycloheptylaminomethanebisphosphonic acid;
(7-dihydro-1-pyrindine)methane bisphosphonic acid;
(7-dihydro-1-pyrindine)hydroxymethane bisphosphonic acid;
(6-dihydro-2-pyrindine)hydroxymethanebisphosphonic acid;
2-(6-pyrolopyridine)-1-hydroxyethane-1,1-bisphosphonic acid;
octahydro-1,1-dimethyl-5,5-diphosphono-1-pyrindinium salt;
octahydro-2,2-dimethyl-5,5-diphosphono-2-pyrindinium salt;
octahydro-1,1-dimethyl-6,6-diphosphono-1-pyrindinium salt;
octahydro-2,2-methyl-6,6-diphosphono-2-pyrindinium salt;
octahydro-1,1-dimethyl-7,7-diphosphono-1-pyrindinium salt;
octahydro-2,2-dimethyl-7,7-diphosphono-2-pyrindinium salt;
octahydro-5,5-diphosphono-1,1,2-trimethyl-1-pyrindinium salt;
octahydro-1,3-diethyl-2,2-dimethyl-5,5-diphosphono-2-pyrindinium salt;
octahydro-1,1-dimethyl-6,6-diphosphono-7-hydroxy-1-pyrindinium salt;
octahydro-2,2-dimethyl-6,6-diphosphono-4-methoxy-2-pyrindinium salt;
octahydro-7,7-diphosphono-1-ethyl-1-methyl-5-vinyl-1-pyrindinium salt;
octahydro-2,2-dimethyl-1-(dimethylamino)-7,7-diphosphono-2-pyrindinium salt;
octahydro-2-(3,4-dichlorophenyl)-1,1-dimethyl-7,7-diphosphono-1-pyrindinium salt;
octahydro-1,1-diethyl-2-(p-dimethylaminophenyl)-7,7-diphosphono-1-pyrindinium salt;
octahydro-4-chloro-1,1-diethyl-6,6-diphosphono-1-pyrindinium salt;
octahydro-4-amino-6,6-diphosphono-1-ethyl-1-propyl-1-pyrindinium salt;
octahydro-7-carboxy-6,6-diphosphono-1,1-dipropyl-1-pyrindinium salt;
octahydro-5-carboxymethylester)-1,1-dimethyl-6,6-diphosphono-1-pyrindinium salt;
octahydro-2,2-diethyl-6,6-diphosphono-4-hydroxy-2-pyrindinium salt;
octahydro-5,5-diphosphono-2-ethyl-7-(ethylketone)-2-methyl-2-pyrindinium salt;
octahydro-1,1-dimethyl-6,6-diphosphono-4-nitro-1-pyrindinium salt;
octahydro-1,1-dimethyl-5,5-diphosphono-1-pyrindinium salt;
octahydro-2,2-dimethyl-5,5-diphosphono-2-pyrindinium salt;
octahydro-1,1-dimethyl-6,6-diphosphono-1-pyrindinium salt;
octahydro-2,2-methyl-6,6-diphosphono-2-pyrindinium salt;
octahydro-1,1-dimethyl-7,7-diphosphono-1-pyrindinium salt;
octahydro-2,2-dimethyl-7,7-diphosphono-2-pyrindinium salt;
octahydro-6,6-diphosphono-1,1,2-trimethyl-1-pyrindinium salt;
octahydro-4-amino-1,1-dimethyl-6,6-diphosphono-1-pyrindinium salt;
2-(2-hydroxy-2,2-diphosphonoethyl)-1,1-dimethylpiperidinium iodide salt;
3-(2-hydroxy-2,2-diphosphonoethyl)-1-methylpyridinium iodide;
3-(2-hydroxy-2,2-diphosphonoethyl)1-methylpyridinium hydroxide;
3-(2,2-diphosphonoethyl)-1-ethylpyridinium chloride;
3-(2,2-diphosphonoethyl)-1-(2-mercaptoethyl) pyridinium chloride;
2-(2-hydroxy-2,2-diphosphonoethyl)-1-methylpyridinium hydroxide;
3-(3-hydroxy-3,3-diphosphonopropyl)-1-methylpyridinium hydroxide;
3-(2,2-diphosphono-2-hydroxyethyl)-1,1-dimethylpiperidinium iodide salt;
3-(2,2-diphosphonoethyl)-1-heptylpyridinium chloride;
3-(2,2-diphosphonoethyl)-1-methylpyridinium chloride;
3-(2,2-phosphonomethylphosphinoethyl)-1-methylpyridinium iodide;
3-(2-phosphono-2-sulfonoethyl)-1-methylpyridinium chloride;
3-(2-carboxy-2-phosphonoethyl)-1-methylpyridinium chloride;
2-diphosphonomethyl-1,1-dimethylpiperidinium chloride;
3-diphosphonomethyl-1,1-dimethylpiperidinium chloride;

4-diphosphonomethyl-1,1-dimethylpiperidinium chloride;

2-(2,2-diphosphonoethyl)-1,1-dimethylpiperidinium chloride;

3-(2,2-diphosphonoethyl)-1, 1-dimethylpiperidinium chloride;

4-(2,2-diphosphonoethyl)-1,1-dimethylpiperidinium chloride;

4-(2,2-diphosphonoethyl)-1,1-dimethylpiperidinium chloride;

2-(2,2-diphosphonoethyl)-1-methyl-1-(2-mercaptoethyl) piperidinium chloride;

3-(2,2-diphosphonoethyl)-1-methyl-1-(2-mercaptoethyl) piperidinium chloride;

4-(2,2-diphosphonoethyl)-1-methyl-1-(2-mercaptoethyl) piperidinium chloride;

2-[2,2-diphosphono-1-(2-mercaptoethyl)ethyl]-1,1-dimethylpiperidinium chloride;

3-[2,2-diphosphono-1-(3-mercaptopropyl)ethyl]-1,1-dimethylpiperidinium chloride;

4-[2,2-diphosphono-1-(2-acetylthioethyl)ethyl]-1,1-dimethylpiperidinium chloride;

2-(2,2-diphosphono-2-hydroxyethyl)-1,1-dimethylpiperidinium chloride;

3-(2,2-diphosphono-2-hydroxyethyl)-1,1-dimethylpiperidinium chloride;

4-(2,2-diphosphono-2-hydroxyethyl)-1,1-dimethylpiperidinium chloride;

2-(2,2-diphosphono-2-hydroxyethyl)-1,1,3-trimethylpiperidinium chloride;

2-(2,2-diphosphono-2-hydroxyethyl)-1,1,5-trimethylpiperidinium chloride;

2-(2,2-diphosphonoethyl)-1,1,3-trimethylpiperidinium chloride;

2-(2,2-diphosphonoethyl)-1,1,5-trimethylpiperidinium chloride;

2-(3,3-diphosphonopropyl)-1,1-dimethylpiperidinium chloride;

3-(3,3-diphosphonopropyl)-1,1-dimethylpiperidinium chloride;

4-(3,3-diphosphonopropyl)-1,1-dimethylpiperidinium chloride;

2-(3,3-diphosphono-3-hydroxypropyl)-1,1-dimethylpiperidinium chloride;

3-(3,3-diphosphono-3-hydroxypropyl)-1,1-dimethylpiperidinium chloride;

4-(3,3-diphosphono-3-hydroxypropyl)-1,1-dimethylpiperidinium chloride;

2-(2,2-diphosphonopropyl)-1,1-dimethylpiperidinium chloride;

3-(2,2-diphosphonopropyl)-1,1-dimethylpiperidinium chloride;

4-(2,2-diphosphonopropyl)-1,1-dimethylpiperidinium chloride;

2-(2,2-diphosphono-2-aminoethyl)-1,1-dimethylpiperidinium chloride;

3-(2,2-diphosphono-2-aminoethyl)-1,1-dimethylpiperidinium chloride;

4-(2,2-diphosphono-2-aminoethyl)-1,1-dimethylpiperidinium chloride;

2-(2,2-diphosphono-2-aminoethyl)-1,1,3-trimethylpiperidinium chloride;

2-(2,2-diphosphono-2-aminoethyl)-1,1,3-trimethylpiperidinium chloride;

3-(2,2-diphosphono-2-aminoethyl)-1,1,5-trimethylpiperidinium chloride;

2-(2,2-diphosphono-2-(methylamino)ethyl)-1,1,-dimethylpiperidinium chloride;

2-(4,4-diphosphono-4-hydroxybutyl)-1,1,3-trimethylpiperidinium chloride;

2-(4,4-diphosphono-4-hydroxybutyl)-1,1-dimethylpiperidinium chloride;

2-(2,2-diphosphono-2-hydroxyethyl)-3-carboxy-1,1-dimethylpiperidinium chloride;

2-(2,2-diphosphono-2-hydroxyethyl)-5-carboxy-1,1-dimethylpiperidinium chloride;

2-(2,2-diphosphonoethyl)-1-methylpyrimidinium chloride;

4-(2,2-diphosphonoethyl)-1-methylpyrimidinium chloride;

2-(2,2-diphosphono-2-hydroxyethyl)-1-methylpyrimidinium chloride;

4-(2,2-diphosphono-2-hydroxyethyl)-1-methylpyrimidinium chloride;

2-(3,3-diphosphonopropyl)-1-methylpyrimidinium chloride;

4-(3,3-diphosphonopropyl)-1-methylpyrimidinium chloride;

2-(3,3-diphosphono-1-hydroxypropyl)-1-methylpyrimidinium chloride;

4-(3,3-diphosphono-1-hydroxypropyl)-1-methylpyrimidinium chloride;

2-(2,2-diphosphono-2-aminoethyl)-1-methylpyrimidinium chloride;

3-[(diphosphonomethyl)oxo]-1,1-dimethylpiperidinium chloride;

4-[(diphosphonomethyl)oxo]-1,1-dimethylpiperidinium chloride;

3-[(2,2-diphosphonoethyl)oxo]-1,1-dimethylpiperidinium chloride;

4-[(2,2-diphosphonoethyl)oxo]-1,1-dimethylpiperidinium chloride;

3-[(diphosphonomethyl)thio]-1,1-dimethylpiperidinium chloride;

4-[(diphosphonomethyl)thio]-1,1-dimethylpiperidinium chloride;

3-(2-hydroxy-2,2-diphosphonoethyl)-1-methylpyridinium iodide;

3-(2-hydroxy-2,2-diphosphonoethyl)-1-methylpyridinium hydroxide;

3-(2,2-diphosphonoethyl)-1-(2-mercaptoethyl) pyridinium chloride;

2-(2-hydroxy-2,2-diphosphonoethyl)-1,1-dimethylpiperidinium iodide salt;

3-(2,2-diphosphono-2-hydroxyethyl)-1,1-dimethylpiperidinium iodide salt;

3-(2,2-diphosphonoethyl)-1-heptylpyridinium chloride;

3-(2,2-diphosphonoethyl)-1-methylpyridinium chloride;

2-(2,2-diphosphonoethyl)-1,1-dimethylpiperidinium chloride;

3-(2,2-diphosphonoethyl)-1,1-dimethylpiperidinium chloride;

4-(2,2-diphosphonoethyl)-1,1-dimethylpiperidinium chloride;

2-(2,2-diphosphono-2-hydroxyethyl)-1,1-dimethylpiperidinium chloride;
3-(2,2-diphosphono-2-hydroxyethyl)-1,1-dimethylpiperidinium chloride;
4-(2,2-diphosphono-2-hydroxyethyl)-1,1-dimethylpiperidinium chloride;
2-(2,2-diphosphono-2-hydroxyethyl)-1,1,3-trimethylpiperidinium chloride;
2-(2,2-diphosphono-2-hydroxyethyl)-1,1,5-trimethylpiperidinium chloride;
2-[2,2-diphosphono-1-(2-mercaptoethyl)ethyl]-1,1-dimethylpiperidinium chloride;
3-[2,2-diphosphono-1-(3-mercaptopropyl)ethyl]-1,1-dimethylpiperidinium chloride;
2-(2,2-diphosphonoethyl)-1-methyl-1-(2-mercaptoethyl)piperidinium chloride;
3-(2,2-diphosphonoethyl)-1-methyl-1-(2-mercaptoethyl)piperidinium chloride;
4-(2,2-diphosphonoethyl)-1-methyl-1-(2-mercaptoethyl)piperidinium chloride;
3-(2-hydroxy-2,2-diphosphonoethyl)-1-methylpyridinium iodide;
3-(2-hydroxy-2,2-diphosphonoethyl)-1-methylpyridinium hydroxide;
3-(2,2-diphosphonoethyl)-1-(2-mercaptoethyl)pyridinium chloride;
2-[2,2-diphosphono-1-(2-mercaptoethyl)ethyl]-1,1-dimethylpiperidinium chloride;
3-[2,2-diphosphono-1-(3-mercaptopropyl)ethyl]-1,1-dimethylpiperidinium chloride;
2-(2,2-diphosphonoethyl)-1-methyl-1-(2-mercaptoethyl)piperidinium chloride;
3-(2,2-diphosphonoethyl)-1-methyl-1-(2-mercaptoethyl)piperidinium chloride;
N-(4-hydroxy-4,4-diphosphonobutyl)-N,N,N-trimethyl ammonium iodide;
N-(3-hydroxy-3,3-diphosphonopropyl)-N,N-dimethyl-N-pentyl ammonium iodide;
N-(3-hydroxy-3,3-diphosphonopropyl)-N,N,N-trimethyl ammonium iodide;
N-cycloheptyl-N,N-dimethyl-N-(diphosphonomethyl) ammonium iodide;
N-(2-acetylthioethyl)-N-(4-hydroxy-4,4-diphosphonobutyl)-N,N-dimethyl ammonium bromide;
N-(2-acetylthioethyl)-N-(3-hydroxy-3,3-diphosphonopropyl)-N-methyl-N-pentyl ammonium bromide;
N-(4-hydroxy-4,4-diphosphonobutyl)-N-(3-mercaptopropyl)-N,N-dimethyl ammonium chloride;
N-(4-hydroxy-4,4-diphosphonobutyl)-N-(mercaptomethyl)-N,N-dimethyl ammonium chloride;
N-(4-hydroxy-4,4-diphosphonobutyl)-N-(4-methoxybutyl)-N,N-dimethyl ammonium chloride;
N-(4-hydroxy-2-mercapto-4,4-diphosphonobutyl)-N,N,N-trimethyl ammonium chloride;
N-(4-hydroxy-2-acetylthio-4,4-diphosphonobutyl)-N,N,N-trimethyl ammonium chloride;
N-(3-hydroxy-2-mercapto-3,3-diphosphonopropyl)-N,N-dimethyl-N-pentyl ammonium chloride;
N-(3-hydroxy-2-acetylthio-3,3-diphosphonopropyl)-N,N-dimethyl-N-pentyl ammonium chloride;
N-(3-hydroxy-3,3-diphosphonopropyl)-N-methyl-N-pentyl-N-(2-(3-pyridyl)ethyl) ammonium chloride;
N-cycloheptyl-N-(2-mercaptoethyl)-N-methyl-N-(diphosphonomethyl) ammonium chloride;
N-cycloheptyl-N-(mercaptomethyl)-N-methyl-N-(diphosphonomethyl) ammonium chloride;
N,N-dimethyl-N-(4,4-diphosphonobutyl)-N-(2-(3-piperidinyl)ethyl) ammonium chloride;
[2-[(2,2-dimethyl-1-oxopropyl)thio]ethylidene]bis[phosphonic acid];
[2-(benzoylthio)ethylidene]bis[phosphonic acid];
[2-(p-methoxy-benzoylthio)ethylidene]bis[phosphonic acid];
[2-(p-amino-benzoylthio)ethylidene]bis[phosphonic acid];
[2-(acetylthio)ethylidene]bis[phosphonic acid] disodium Salt;
[2-mercapto-2-(phenyl)ethylidene]bis[phosphonic acid];
[2-mercapto-2-(o-aminophenyl)ethylidene]bis[phosphonic acid];
[2-mercapto-2-(m-aminophenyl)ethylidene]bis[phosphonic acid];
[2-mercapto-2-(p-aminophenyl)ethylidene]bis[phosphonic acid];
[2-acetylthio-2-(phenyl)ethylidene]bis[phosphonic acid];
[3-mercapto-1-hydroxybutylidene]bis[phosphonic acid];
[3-mercapto3-methyl-1-hydroxybutylidene]bis[phosphonic acid];
[4-amino-3-mercapto-1-hydroxybutylidene]bis[phosphonic acid];
[4-amino-2-mercapto-1-hydroxybutylidene]bis[phosphonic acid];
[2-amino-1-hydroxy-3-mercapto-3-methylbutylidene]bis[phosphonic acid];
[2-amino-1-hydroxy-3-acetylthio-3-methylbutylidene]bis[phosphonic acid];
1-[(hydroxy)methylphosphinyl]-2-mercaptoethylphosphonic acid;
[2-mercapto-2-methylpropylidene]bis[phosphonic acid];
[2-(acetylthio)-2-methylpropylidene]bis[phosphonic acid] disodium salt;
[1-hydroxy-2-(2-acetylthiocyclohexyl)ethylidene]bis[phosphonic acid];
[1-hydroxy-2-(3-acetylthiocyclohexyl)ethylidene]bis[phosphonic acid];
[1-hydroxy-2-(4-acetylthiocyclohexyl)ethylidene]bis[phosphonic acid];
[1-hydroxy-2-(2-mercaptocyclohexyl)ethylidene]bis[phosphonic acid];
[1-hydroxy-2-(3-mercaptocyclohexyl)ethylidene]bis[phosphonic acid];
[1-hydroxy-2-(4-mercaptocyclohexyl)ethylidene]bis[phosphonic acid];
[1-hydroxy-2-(2-(3-mercaptopropyl)cyclohexyl)ethylidene]bis[phosphonic acid];
[1-hydroxy-2-(3-(2-mercaptoethyl)cyclohexyl)ethylidene]bis[phosphonic acid];
[1-hydroxy-2-(2-acetylthiocyclopentyl)ethylidene]bis[phosphonic acid];
[1-hydroxy-2-(3-acetylthiocyclopentyl)ethylidene]bis[phosphonic acid];

[1-hydroxy-2-(2-mercaptocyclopentyl)ethylidene]bis[phosphonic acid];
[1-hydroxy-2-(3-mercaptocyclopentyl)ethylidene]bis[phosphonic acid];
[1-hydroxy-2-(2-(2-mercaptoethyl)cyclopentyl)ethylidene]bis[phosphonic acid];
[1-hydroxy-2-(2-(3-mercaptopropyl)cyclopentyl)ethylidene]bis[phosphonic acid];
[2-mercapto-5-phenylpentylidene]bis[phosphonic acid];
[2-mercapto-5-(o-aminophenyl)pentylidene]bis[phosphonic acid];
[2-mercapto-5-(m-aminophenyl)pentylidene]bis[phosphonic acid];
[2-mercapto-5-(p-aminophenyl)pentylidene]bis[phosphonic acid];
[2-mercapto-5-phenylbutylidene]bis[phosphonic acid];
[2-mercapto-5-(o-aminophenyl)butylidene]bis[phosphonic acid];
[2-mercapto-5-(m-aminophenyl)butylidene]bis[phosphonic acid];
[2-mercapto-5-(p-aminophenyl)butylidene]bis[phosphonic acid];
[2-acetylthio-5-phenylpentylidene]bis[phosphonic acid];
[2-acetylthio-5-(p-aminophenyl)pentylidene]bis[phosphonic acid];
[3-(3-furfuryl)-2-mercaptoethylidene]bis[phosphonic acid];
[3-cyclohexyl-2-mercaptopropylidene]bis[phosphonic acid];
octahydro-2-mercapto-1-pyrindine-5,5-bisphosphonic acid;
octahydro-3-mercapto-1-pyrindine-5,5-bisphosphonic acid;
octahydro-4-mercapto-1-pyrindine-5,5-bisphosphonic acid;
octahydro-3-thiomethyl-1-pyrindine-5,5-bisphosphonic acid;
octahydro-3-thioethyl-1-pyrindine-5,5-bisphosphonic acid;
octahydro-7-(2-mercaptoethyl)-1-pyrindine-6,6-bisphosphonic acid;
octahydro-3-thiopropyl-1-pyrindine-5,5-bisphosphonic acid;
octahydro-3-thiobutyl-1-pyrindine-5,5-bisphosphonic acid;
octahydro-2-thioethyl-1-pyrindine-5,5-bisphosphonic acid;
octahydro-4-thiopropyl-1-pyrindine-5,5-bisphosphonic acid;
octahydro-2-methoxy-4-thiobutyl-1-pyrindine-5,5-bisphosphonic acid;
octahydro-2-mercapto-1-pyrindine-6,6-bisphosphonic acid;
octahydro-3-mercapto-1-pyrindine-6,6-bisphosphonic acid;
octahydro-4-mercapto-1-pyrindine-6,6-bisphosphonic acid;
octahydro-3-thiomethyl-1-pyrindine-6,6-bisphosphonic acid;
octahydro-3-thioethyl-1-pyrindine-6,6-bisphosphonic acid;
octahydro-3-thiopropyl-1-pyrindine-6,6-bisphosphonic acid;
octahydro-3-thiobutyl-1-pyrindine-6,6-bisphosphonic acid;
octahydro-2-thioethyl-1-pyrindine-6,6-bisphosphonic acid;
octahydro-4-thiopropyl-1-pyrindine-6,6-bisphosphonic acid;
octahydro-2-methoxy-4-thiobutyl-1-pyrindine-6,6-bisphosphonic acid;
octahydro-2-mercapto-1-pyrindine-7,7-bisphosphonic acid;
octahydro-3-mercapto-1-pyrindine-7,7-bisphosphonic acid;
octahydro-4-mercapto-1-pyrindine-7,7-bisphosphonic acid;
octahydro-3-thiomethyl-1-pyrindine-7,7-bisphosphonic acid;
octahydro-3-thioethyl-1-pyrindine-7,7-bisphosphonic acid;
octahydro-3-thiopropyl-1-pyrindine-7,7-bisphosphonic acid;
octahydro-3-thiobutyl-1-pyrindine-7,7-bisphosphonic acid;
octahydro-2-thioethyl-1-pyrindine-7,7-bisphosphonic acid;
octahydro-4-thiopropyl-1-pyrindine-7,7-bisphosphonic acid;
octahydro-2-methoxy-4-thiobutyl-1-pyrindine-7,7-bisphosphonic acid;
octahydro-1-mercapto-2-pyrindine-5,5-bisphosphonic acid;
octahydro-3-mercapto-2-pyrindine-5,5-bisphosphonic acid;
octahydro-4-mercapto-2-pyrindine-5,5-bisphosphonic acid;
octahydro-4-thiomethyl-2-pyrindine-5,5-bisphosphonic acid;
octahydro-4-thioethyl-2-pyrindine-5,5-bisphosphonic acid;
octahydro-4-thiopropyl-2-pyrindine-5,5-bisphosphonic acid;
octahydro-4-thiobutyl-2-pyrindine-5,5-bisphosphonic acid;
octahydro-3-thioethyl-2-pyrindine-5,5-bisphosphonic acid;
octahydro-1-thiopropyl-2-pyrindine-5,5-bisphosphonic acid;
octahydro-1-methoxy-4-thiobutyl-2-pyrindine-5,5-bisphosphonic acid;
octahydro-4-amino-1-thiobutyl-2-pyrindine-5,5-bisphosphonic acid;
octahydro-4-hydroxy-4-thiobutyl-2-pyrindine-5,5-bisphosphonic acid;
octahydro-1-mercapto-2-pyrindine-6,6-bisphosphonic acid;
octahydro-3-mercapto-2-pyrindine-6,6-bisphosphonic acid;
octahydro-4-mercapto-2-pyrindine-6,6-bisphosphonic acid;
octahydro-4-thiomethyl-2-pyrindine-6,6-bisphosphonic acid;

octahydro-4-thioethyl-2-pyrindine-6,6-bisphosphonic acid;
octahydro-4-thiopropyl-2-pyrindine-6,6-bisphosphonic acid;
octahydro-4-thiobutyl-2-pyrindine-6,6-bisphosphonic acid;
octahydro-3-thioethyl-2-pyrindine-6,6-bisphosphonic acid;
octahydro-1-thiopropyl-2-pyrindine-6,6-bisphosphonic acid;
octahydro-1-methoxy-4-thiobutyl-2-pyrindine-6,6-bisphosphonic acid;
octahydro-4-amino-1-thiobutyl-2-pyrindine-6,6-bisphosphonic acid;
octahydro-4-hydroxy-4-thiobutyl-2-pyrindine-6,6-bisphosphonic acid;
octahydro-1-mercapto-2-pyrindine-7,7-bisphosphonic acid;
octahydro-3-mercapto-2-pyrindine-7,7-bisphosphonic acid;
octahydro-4-mercapto-2-pyrindine-7,7-bisphosphonic acid;
octahydro-4-thiomethyl-2-pyrindine-7,7-bisphosphonic acid;
octahydro-4-thoctahydro-3-amino-5-(1-mercapto-1-methyl)ethyl-1-pyrindine-octahydro-7-mercapto-1-pyrindine-6,6-bisphosphonic acid;
octahydro-5-(2-thioethyl)-1-pyrindine-6,6-bisphosphonic acid;
octahydro-7-thiomethyl-1-pyrindine-6,6-bisphosphonic acid;
octahydro-7-thiobutyl-1-pyrindine-6,6-bisphosphonic acid;
octahydro-3-amino-7-mercapto-1-pyrindine-6,6-bisphosphonic acid;
octahydro-3-amino-5-thiopropyl-1-pyrindine-6,6-bisphosphonic acid;
octahydro-3-methoxy-7-(1-mercapto-1-methyl)ethyl-1-pyrindine-6,6-bisphosphonic acid;
octahydro-3-amino-5-(1-mercapto-1-methyl)ethyl-1-pyrindine-6,6-bisphosphonic acid;
octahydro-4-thiopropyl-2-pyrindine-7,7-bisphosphonic acid;
octahydro-4-thiobutyl-2-pyrindine-7,7-bisphosphonic acid;
octahydro-3-thioethyl-2-pyrindine-7,7-bisphosphonic acid;
octahydro-1-thiopropyl-2-pyrindine-7,7-bisphosphonic acid;
octahydro-1-methoxy-4-thiobutyl-2-pyrindine-7,7-bisphosphonic acid;
octahydro-4-amino-1-thiobutyl-2-pyrindine-7,7-bisphosphonic acid;
octahydro-4-hydroxy-4-thiobutyl-2-pyrindine-7,7-bisphosphonic acid;
octahydro-7-(1-mercapto-1-methyl)ethyl-1-pyrindine-5,5-bisphosphonic acid;
octahydro-3-hydroxy-7-thiobutyl-1-pyrindine-5,5-bisphosphonic acid;
octahydro-3-dimethylamino-6-thiomethyl-1-pyrindine-5,5-bisphosphonic acid;
octahydro-7-thioethyl-1-pyrindine-5,5-bisphosphonic acid;
octahydro-6-hydroxy-7-thiopropyl-1-pyrindine-5,5-bisphosphonic acid;
octahydro-6-(1-mercapto-1-methyl)ethyl-1-pyrindine-5,5-bisphosphonic acid;
dihydro-2-mercapto-1-pyrindine-6,6-bisphosphonic acid;
dihydro-3-mercapto-1-pyrindine-6,6-bisphosphonic acid;
dihydro-4-mercapto-1-pyrindine-6,6-bisphosphonic acid;
dihydro-3-thiomethyl-1-pyrindine-6,6-bisphosphonic acid;
dihydro-3-thioethyl-1-pyrindine-6,6-bisphosphonic acid;
dihydro-3-thiopropyl-1-pyrindine-6,6-bisphosphonic acid;
dihydro-3-thiobutyl-1-pyrindine-6,6-bisphosphonic acid;
dihydro-2-thioethyl-1-pyrindine-6,6-bisphosphonic acid;
dihydro-4-thiopropyl-1-pyrindine-6,6-bisphosphonic acid;
dihydro-2-methoxy-4-thiobutyl-1-pyrindine-6,6-bisphosphonic acid;
dihydro-1-mercapto-2-pyrindine-6,6-bisphosphonic acid;
dihydro-3-mercapto-2-pyrindine-6,6-bisphosphonic acid;
dihydro-4-mercapto-2-pyrindine-6,6-bisphosphonic acid;
dihydro-4-thiomethyl-2-pyrindine-6,6-bisphosphonic acid;
dihydro-4-thioethyl-2-pyrindine-6,6-bisphosphonic acid;
dihydro-4-thiopropyl-2-pyrindine-6,6-bisphosphonic acid;
dihydro-4-thiobutyl-2-pyrindine-6,6-bisphosphonic acid;
dihydro-3-thioethyl-2-pyrindine-6,6-bisphosphonic acid;
dihydro-1-thiopropyl-2-pyrindine-6,6-bisphosphonic acid;
dihydro-1-methoxy-4-thiobutyl-2-pyrindine-6,6-bisphosphonic acid;
dihydro-4-amino-1-thiobutyl-2-pyrindine-6,6-bisphosphonic acid;
dihydro-4-hydroxy-4-thiobutyl-2-pyrindine-6,6-bisphosphonic acid;
dihydro-7-mercapto-1-pyrindine-6,6-bisphosphonic acid;
dihydro-5-mercapto-1-pyrindine-6,6-bisphosphonic acid;
dihydro-7-thiomethyl-1-pyrindine-6,6-bisphosphonic acid;
dihydro-7-thiobutyl-1-pyrindine-6,6-bisphosphonic acid;
dihydro-3-amino-7-mercapto-1-pyrindine-6,6-bisphosphonic acid;
dihydro-3-amino-5-thiopropyl-1-pyrindine-6,6-bisphosphonic acid;
dihydro-3-methoxy-7-(1-mercapto-1-methyl)ethyl-1-pyrindine-6,6-bisphosphonic acid;
dihydro-1-mercapto-2-pyrindine-7,7-bisphosphonic acid;
dihydro-3-mercapto-2-pyrindine-7,7-bisphosphonic acid;
dihydro-4-mercapto-2-pyrindine-7,7-bisphosphonic acid;
dihydro-4-thiomethyl-2-pyrindine-7,7-bisphosphonic acid;
dihydro-4-thioethyl-2-pyrindine-7,7-bisphosphonic acid;
dihydro-4-thiopropyl-2-pyrindine-7,7-bisphosphonic acid;
dihydro-4-thiobutyl-2-pyrindine-7,7-bisphosphonic acid;
dihydro-3-thioethyl-2-pyrindine-7,7-bisphosphonic acid;
dihydro-1-thiopropyl-2-pyrindine-7,7-bisphosphonic acid;
dihydro-1-methoxy-4-thiobutyl-2-pyrindine-7,7-bisphosphonic acid;

dihydro-4-amino-1-thiobutyl-2-pyrindine-7,7-bisphosphonic acid;
dihydro-4-hydroxy-4-thiobutyl-2-pyrindine-7,7-bisphosphonic acid;
dihydro-2-mercapto-1-pyrindine-7,7-bisphosphonic acid;
dihydro-3-mercapto-1-pyrindine-7,7-bisphosphonic acid;
dihydro-4-mercapto-1-pyrindine-7,7-bisphosphonic acid;
dihydro-3-thiomethyl-1-pyrindine-7,7-bisphosphonic acid;
dihydro-3-thioethyl-1-pyrindine-7,7-bisphosphonic acid;
dihydro-3-thiopropyl-1-pyrindine-7,7-bisphosphonic acid;
dihydro-3-thiobutyl-1-pyrindine-7,7-bisphosphonic acid;
dihydro-2-thioethyl-1-pyrindine-7,7-bisphosphonic acid;
dihydro-4-thiopropyl-1-pyrindine-7,7-bisphosphonic acid;
dihydro-2-methoxy-4-thiobutyl-1-pyrindine-7,7-bisphosphonic acid;
dihydro-7-(1-mercapto-1-methyl)ethyl-1-pyrindine-5,5-bisphosphonic acid;
dihydro-3-hydroxy-7-thiobutyl-1-pyrindine-5,5-bisphosphonic acid;
dihydro-3-dimethylamino-6-thiomethyl-1-pyrindine-5,5-bisphosphonic acid;
dihydro-7-thioethyl-1-pyrindine-5,5-bisphosphonic acid;
dihydro-6-hydroxy-7-thiopropyl-1-pyrindine-5,5-bisphosphonic acid;
dihydro-6-(1-mercapto-1-methyl)ethyl-1-pyrindine-5,5-bisphosphonic acid;
dihydro-1-mercapto-2-pyrindine-5,5-bisphosphonic acid;
dihydro-3-mercapto-2-pyrindine-5,5-bisphosphonic acid;
dihydro-4-mercapto-2-pyrindine-5,5-bisphosphonic acid;
dihydro-4-thiomethyl-2-pyrindine-5,5-bisphosphonic acid;
dihydro-4-thioethyl-2-pyrindine-5,5-bisphosphonic acid;
dihydro-4-thiopropyl-2-pyrindine-5,5-bisphosphonic acid;
dihydro-4-thiobutyl-2-pyrindine-5,5-bisphosphonic acid;
dihydro-3-thioethyl-2-pyrindine-5,5-bisphosphonic acid;
dihydro-1-thiopropyl-2-pyrindine-5,5-bisphosphonic acid;
dihydro-1-methoxy-4-thiobutyl-2-pyrindine-5,5-bisphosphonic acid;
dihydro-4-amino-1-thiobutyl-2-pyrindine-5,5-bisphosphonic acid;
dihydro-4-hydroxy-4-thiobutyl-2-pyrindine-5,5-bisphosphonic acid;
dihydro-2-mercapto-1-pyrindine-5,5-bisphosphonic acid;
dihydro-3-mercapto-1-pyrindine-5,5-bisphosphonic acid;
dihydro-4-mercapto-1-pyrindine-5,5-bisphosphonic acid;
dihydro-3-thiomethyl-1-pyrindine-5,5-bisphosphonic acid;
dihydro-3-thioethyl-1-pyrindine-5,5-bisphosphonic acid;
dihydro-3-thiopropyl-1-pyrindine-5,5-bisphosphonic acid;
dihydro-3-thiobutyl-1-pyrindine-5,5-bisphosphonic acid;
dihydro-2-thioethyl-1-pyrindine-5,5-bisphosphonic acid;
dihydro-4-thiopropyl-1-pyrindine-5,5-bisphosphonic acid;
dihydro-2-methoxy-4-thiobutyl-1-pyrindine-5,5-bisphosphonic acid;
[(5-[mercaptomethyl]-2-piperidinyl)methylene]bis[phosphonic acid;
[(5-mercaptomethyl-3-piperidinyl]methylene]bis[phosphonic acid;
[(5-mercapto-2-piperidinyl)methylene]bis[phosphonic acid; [(5-[4-mercaptobutyl]-2-piperidinyl)methylene]bis[phosphonic acid;
[(5-mercapto-3-piperidinyl)methylene]bis[phosphonic acid;
[(5-[5-mercaptopentyl]-3-piperidinyl)methylene]bis[phosphonic acid;
[(5-[2-mercaptoethyl]-4-piperidinyl)methylene]bis[phosphonic acid;
[(5-mercapto-4-piperidinyl)methylene]bis[phosphonic acid;
[2-(5-mercapto-2-piperidinyl)ethylidene]bis[phosphonic acid];
[2-(5-[3-mercaptopropyl]-2-piperidinyl)ethylidene bis[phosphonic acid];
[2-(5-mercapto-3-piperidinyl)ethylidene]bis[phosphonic acid];
[2-(5-mercapto-4-piperidinyl)ethylidene]bis[phosphonic acid];
[2-(5-[4-mercaptobutyl]-2-piperidinyl)ethylidene]bis[phosphonic acid];
[2-(5-mercaptomethyl-3-piperidinyl)ethylidene]bis[phosphonic acid];
[(2-[5-mercapto-2-piperidinyl]-1-hydroxy)ethylidene]bis[phosphonic acid];
[(2-[5-(3-mercaptopropyl)-2-piperidinyl]-1-hydroxy)ethylidene]bis[phosphonic acid] [(2-[5-mercapto-3-piperidinyl]-1-hydroxy)ethylidene]bis[phosphonic acid];
[(2-[5-(2-mercaptoethyl)-3-piperidinyl]-1-hydroxy)ethylidene]-bis[phosphonic acid];
[(2-[5-mercapto-4-piperidinyl]-1-hydroxy)ethylidene]bis[phosphonic acid];
[(2-[5-mercaptomethyl-4-piperidinyl]-1-hydroxy)ethylidene]bis[phosphonic acid];
[(2-[5-mercaptomethyl-3-methyl-2-piperidinyl]-1-hydroxy)-ethylidene]bis[phosphonic acid];
[(2-[5-mercapto-3-methyl-2-piperidinyl]-1-hydroxy)ethylidene]bis[phosphonic acid];
[(2-[3-mercaptomethyl-5-methyl-2-piperidinyl]-1-hydroxy)-ethylidene]bis[phosphonic acid];
[2-(5-mercaptomethyl-3-methyl-2-piperidinyl)-ethylidene]bis[phosphonic acid];
[2-(3-mercaptomethyl-5-methyl-2-piperidinyl)-ethylidene]bis[phosphonic acid];
[3-[5-(mercaptomethyl)-2-piperidinyl]propylidene]bis[phosphonic acid];
[3-[5-(mercaptomethyl)-3-piperidinyl]propylidene]bis[phosphonic acid];
[3-[5-(mercaptomethyl)-4-piperidinyl]propylidene]bis[phosphonic acid];
[3-[5-(mercaptomethyl)-2-piperidinyl]-1-hydroxypropylidene]bis[phosphonic acid];
[3-[5-mercapto-3-piperidinyl]-1-hydroxypropylidene]bis[phosphonic acid];
[3-[5-(4-mercaptobutyl)-4-piperidinyl]-1-hydroxypropylidene]-bis[phosphonic acid];
[2-(3-mercaptomethyl-5-methyl-2-pyridinyl)ethylidene]-bis[phosphonic acid];

[2-(5-[3-mercaptopropyl]-2-methyl-2-piperidinyl) ethylidene]bis[phosphonic acid];

[(2-[5-(2-mercaptopropyl)-2-piperidinyl]-1-amino) ethylidene]bis[phosphonic acid];

[(2-[5-(3-mercaptopropyl)-3-piperidinyl]-1-amino) ethylidene]bis[phosphonic acid];

[2-(5-[3-mercaptopropyl]-4-piperidinyl)-1-aminoethylidene]bis[phosphonic acid];

[(2-[3-methyl-5-(3-mercaptopropyl)-2-piperidinyl]-1-hydroxy)-ethylidene]bis[phosphonic acid];

[(2-[3-amino-5-(3-mercaptopropyl)-2-piperidinyl]-1-hydroxy)ethylidene]bis[phosphonic acid];

[2-[5-mercapto-2-(1,4-diazinyl)]ethylidene)-bis[phosphonic acid];

[2-[5-(3-mercaptopropyl)-2-(1,4-diazinyl)]ethylidene]bis[phosphonic acid];

[2-[5-(3-mercaptopropyl)-2-(1,4-diazinyl)]-1-hydroxyethylidene]bis[phosphonic acid];

[2-[5-mercapto-2-(1,4-diazinyl)]-1-hydroxyethylidene]bis[phosphonic acid];

[2-[5-mercapto-2-(1,3-diazinyl)]ethylidene]bis[phosphonic acid] [2-[5-(3-mercaptopropyl)-2-(1,3-diazinyl)]ethylidene]bis[phosphonic acid];

[2-[5-(3-mercaptopropyl)-2-(1,3-diazinyl)]-1-hydroxyethylidene]bis[phosphonic acid];

[2-[5-mercapto-2-(1,3-diazinyl)]-1-hydroxyethylidene]bis[phosphonic acid];

[(5-[3-mercaptopropyl)-2-piperidinyl)aminomethylene]bis[phosphonic acid];

[(5-mercapto-2-piperidinyl)aminomethylene]bis[phosphonic acid];

[(5-[3-mercaptopropyl]-3-piperidinyl)aminomethylene]bis[phosphonic acid];

[(5-mercapto-3-piperidinyl)aminomethylene]bis[phosphonic acid];

[(5-mercapto-4-piperidinyl)aminomethylene]bis[phosphonic acid];

[(5-[3-mercaptopropyl]-4-piperidinyl)aminomethylene]bis[phosphonic acid];

[(5-mercapto-3-methyl-2-piperidinylidene)aminomethylene]bis[phosphonic acid];

[(5-[3-mercaptopropyl]-3-methyl-2-piperidinylidene)aminomethylene]bis[phosphonic acid];

[2-(5-mercapto-3-methyl-2-piperidinylidene)aminoethylene]bis[phosphonic acid];

[2-(5-[3-mercaptopropyl]-3-methyl-2-piperidinylidene)aminomethylene]bis[phosphonic acid];

[(5-mercapto-2-piperidinylidene)aminomethylene]bis[phosphonic acid];

[(5-[3-mercaptopropyl]-2-piperidinylidene)aminomethylene]bis[phosphonic acid];

[2-(5-mercapto-2-piperidinylidene)aminoethylene]bis[phosphonic acid] [(5-[3-mercaptopropyl]-2-piperidinylidene)aminomethylene]bis[phosphonic acid];

[(5-[3-mercaptopropyl]-2-[1,4-diazinylidene]) aminomethylene]bis[phosphonic acid];

[(5-[3-mercaptopropyl]-2-[1,3-diazinylidene]) aminomethylene)-bis[phosphonic acid];

[(4-[3-mercaptopropyl]-2-[1,3,5-triazinylidene]) aminomethylene]bis[phosphonic acid]; and N-(2'-(1',3'-diazinylidene))-aminomethane diphosphonic acid.

II. Non-Steroidal Anti-Inflammatory Agents (NSAIDS)

The non-steroidal anti-inflammatory agents suitable for use in the methods of treatment for arthritis described herein include all non-steroidal anti-inflammatory drugs (NSAIDs) used to treat undesirable inflammation of body tissues. Suitable NSAIDs for use in the treatment regimens described herein include, but are not limited to, indole-based anti-inflammtory agents (including among others, indomethacin, indoxole and the like); salicylate-based anti-inflammatory agents (including among others, aspirin and the like); phenylacetic acid-based anti-inflammatory drugs (including, among others, fenoprofen, ketoprofen, MK-830 and the like); pyrazolidine-based anti-inflammatory agents (including, among others, phenylbutazone, oxyphenbutazone, and the like); and p-(isobutylphenyl) acetic acid-based anti-inflammatory agents (including, among others,: buprofen, ibufenac, and the like).

The above-described anti-inflammatory compounds are known for use in the treatment of arthritic disorders; see, e.g. (for indole-base compounds) Thompson M. et al., "Further experience with indomethacin in the treatment of rheumatic disorders", *British Medical Journal*, Vol. 1, (1966) pp 80–83; Kelly, M., "Treatment of 193 rheumatic patients with indomethacin, a new antirheumatic drug", *American Geriatric Society*, Vol. 14, (1966), pp 48–55; O'Brien, W. M., "Indomethacin: a survey of clinical trials", *Clinical Pharmacological Therapeutics*, Vol. 9, (1968), pp. 94–107; (for salicylate compounds) REPORT ON RHEUMATIC DISEASES, No. 33, London, The Arthritis and Rheumatism Council, 1968; Hart, F. D., "Control of Pain in rheumatic disorders", *British Medical Journal*, Vol. iii (1968) pp 635–640; Hart, F. D., "Antiinflammatory drugs in the treatment of rheumatic diseases", *Practitioner*, Vol. 205 (1970) pp 597–603; (for p-(isobutylphenyl) acetic acid-based compounds) Boardman et al., "Ibuprofen in the treatment of rheumatoid arthritis and osteoarthritis", *Ann. Rheum. Dis.*, Vol. 26 (1967) pp 560–61; Jasani et al., "Ibuprofen in Rheumatoid Arthritis: Clinical study of analgesic and anti-inflammatory activity", *Ann. Rheum. Dis.*, Vol. 27 (1968) pp 457–62; Chalmers, et al. "Clinical experience with Ibuprofen in the treatment of rheumatoid arthritis", *Ann. Rheum. Dis.*, Vol. 28(5) (1969) pp 513–17.

NSAIDS preferred for use in the methods of treatment described herein include, but are not limited to, salicylates, indomethacin, flurbiprofen, diclofenac, naproxen, piroxicam, tebufelone, and ibuprofen. Other NSAIDs suitable for use herein include, but are not limited to, etodolac, nabumetone, tenidap, alcofenac, antipyrine, aminopyrine, dipyrone, aminopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, salidifamides, sulindac, suprofen, and tolmetin.

In addition to the particular NSAIDs described above, suitable NSAIDS also include any non-steroidal compound used to treat undesirable inflammation of body tissues. Inflammation or the "inflammatory response" is the result of complex interconnected physiological events, including increased vascular permeability, fluid accumulation, and the migration of a changing population of inflammatory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis, and arthritic-like conditions. The inflammatory response is generally believed to be a primary defense mechanism in the body, but unchecked, can become excessive and can result in functional impairment. In fact, as stated hereinabove, it is believed that most of the bone and joint destruction that occurs in arthritic conditions occurs during periods of flare, when inflammation is especially severe.

As stated above, there are numerous side effects associated with taking NSAIDs for prolonged periods, and/or in excessive doses. These common side effects include, but are not limited to, gastrointestinal disorders including gastrointestinal ulcerations, bleeding, and perforations; renal disease; hepatic disease; ocular disturbances; and physiological and psycological central nervous system effects. As stated hereinabove, the daily dosage of NSAID used in the treatment regimens described herein reduce the conventional therapeutic daily dose of a particular NSAID by 20% to 80%, preferably by 30% to 80%, most preferably by 50% to 80%; the proposed dosages suitable for use herein therefore include 20 to 80%, preferably 20 to 70%, most preferably 20 to 50% of the conventional therapeutic dose. Accordingly, in Table I, suitable dosages for the method of treatment described herein for certain preferred NSAIDs are set forth. For ease of comparison, the conventional therapeutic dose (hereinafter CTD) is listed for each preferred NSAID and is set forth as listed in *The Physician's Desk Reference,* 46th Edition (1992) (hereinafter PDR) are listed for each preferred NSAID. Where the PDR lists higher dosages given during "limited periods" (LP) or during active flares (AF), those dosages are listed in a separate column. The NSAID dosages suitable for use as the treatment herein are listed as the "proposed dose" and reflect a reduction of 20% to 80% from the CTD given for that particular NSAID.

TABLE I

| NSAID | CTD$^1$ (mg/day) | AF, LP$^2$ (mg/day) | Proposed Dose (mg/day) |
|---|---|---|---|
| indomethacin | 150–200 | 200–250 | 20–50 |
| diclofenac | 150–200 | — | 50–100 |
| naproxen | 500–1000 | 1500 | 300–500 |
| fenoprofen | 900–2400 | 3200 | 200–800 |
| ibuprofen | 200–1200 | * | 50–150 |
| motrin | 1200–3200 | * | 500–1000 |
| tenedap | 120 | — | 50–100 |
| piroxicam | 20 | — | 5–15 |
| etodolac | 600–1200 | — | 200–400 |
| nectofenamate | 200–400 | — | 50–150 |

$^1$CTD means Conventional Therapeutic Dose as described herein, as set forth in the 1992 Physicians Desk Reference, 46th Edition; denotes total daily dose, to be administered chronically in total mg per day.
$^2$AF, LP means certain higher doses noted for Active Flare (AF) periods or for Limited Periods (LP) noted in the PDR for some NSAIDs.
$^3$Proposed Dose is the dosage suitable for use in the treatment regimens described herein, in total daily dose, (on days when given) in total mg per day.
*Notation indicates flares may require higher doses, no specific dose given.
-Notation indicates no information given.

METHODS OF TREATMENT

This invention provides methods for treating arthritis in a human or other animal subject afflicted with arthritis, especially rheumatoid arthritis or osteoarthritis, comprising one or more sixty (60)-day treatment periods, comprised of an optional NSAID administration regimen and a phosphonate administration regimen, wherein (a) said optional NSAID administration regimen comprises the administration to said subject of NSAIDs at a level of from 20% to 80%, preferably from 20% to 70%, most preferably from 20% to 50%, of conventionally prescribed daily dose on each day that said NSAID is administered; provided that said NSAID is administered in sufficient quantities and on a sufficient number of days to alleviate symptoms of inflammation, and wherein (b) said phosphonate administration regimen comprises the administration to said subject of a phosphonate at a systemic level of from about 0.0005 mgP/kg to about 1.0 mgP/kg per day that said phosphonate is administered; provided that said phosphonate is administered at least 1 day of every said sixty (60)-day treatment period.

The methods of the present invention comprise the treatment of arthritis utilizing the administration of bone-active phosphonates and NSAIDs to a human or other animal subject. Specific compounds and compositions to be used in these processes must, accordingly, be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

Most individuals who suffer from arthritis exhibit alternating periods of flaring characterized by intense pain, swelling, heat and inflammation of the afflicted joints and periods where there is usually some, but considerably less, pain and inflammation. These periods vary in duration and are usually virtually unpredictable. Oftentimes, especially with osteoarthritis, the patient suffers from considerable pain, discomfort, and lessened range of motion for a prolonged period of time before visiting a physician. The first visit to a physician often results from the occurrence of an active flare of the disease which is so painful that the individual finally seeks medical treatment.

The current therapy of arthritis generally consists of initial therapy with NSAIDS to relieve pain and inflammation. In many cases, the dose initially prescribed is increased because symptoms are not relieved as desired. In many instances, a particular NSAID administered at the highest dose indicated has little or no effect on the pain and inflammation. At this time, the physician will often then prescribe another NSAID, repeating the same pattern of increasing the dose as before. Generally, even after a satisfactory NSAID (at a safe and effective dose) is found, and then for the remainder of the patient's life, the arthritic patient will be under constant administration of NSAIDs. The side effects of chronic NSAID therapy include gastrointestinal toxicity (bleeding, ulceration and perforation), renal toxicity (papillary necrosis, reduction in renal blood flow), ocular effects (corneal deposits and retinal disturbances), and physiological and psychological central nervous system effects.

The sixty (60)-day NSAID treatment regimen described hereinabove may be varied and/or repeated over and over, followed one immediately after the other, or with intermittent periods of no or other therapy. It is the ultimate aim in the treatment of each patient that the dosage of NSAIDs (daily dose) and/or days during treatment period when NSAID is dosed (days dosed) is reduced. NSAIDs should ultimately only be administered in the event of an ensuing flare period, preferably at the first sign of aggravated condition, such as increased inflammation and/or pain. The phosphonate compound is given to inhibit bone and hard tissue destruction in the intraarticular area of the joint, which then allows repair of the subchondral bone. With the passage of time, this should result in a substantially reduced incidence of active flare periods; since they are currently thought to be the periods when most damage and destruction occurs which will ultimately in and of itself reduce damage. Since the NSAID active agent and the phosphonate active agent work together synergistically, the NSAID dosage (and possibly the phosphonate dosage) are steadily and consistently reduced so that the maintenance therapy ultimately evolves into successive treatment periods consisting solely of phosphonate therapy; it would accordingly be most preferred that NSAIDs are totally withdrawn with the phosphonate dosed once only during the sixty (60)-day treatment period. For most patients, the ultimate withdrawal of NSAIDs would be accomplished after may treatment periods wherein the NSAID administration (days dosed and/or daily dose) was constantly and consistently reduced.

Accordingly, the sixty (60)-day treatment period is comprised of a separate administration regimen for each active, i.e. one for the NSAID, which is optional, and one for the phosphonate compound. The NSAID is optionally administered during the sixty (60)-day treatment period in order to maintain the physiological effect of the NSAID in the subject being treated. In other words, the NSAID is given only when necessary to relieve inflammation, edema, and pain in the individual. When necessary, the NSAID may be given every day of said sixty (60)-day treatment period, or every other day, or every third day, or every fourth day, or every fifth day, or every sixth day of said sixty (60)-day treatment period. It may be more desirable to give NSAID for the first week at one dose, switch to other doses for the second, third, and/or fourth weeks. It may be desirable to administer one type of NSAID on some treatment days and another type on other treatment days. It may also be desirable to administer the same and/or different NSAID at different doses on different days of the treatment period. The only limitation in the optional NSAID regimen is that the NSAID should be given when needed to reduce inflammation, edema and pain and to prevent and/or alleviate active flare periods. The daily dosage of NSAIDs required is 20% to 80%, preferably 30% to 80%, most preferably 50% to 80%, of the conventional therapeutic dosage as defined herein.

In addition, a phosphonate must be given at least one day of every sixty (60)-day treatment period. For example, a phosphonate may be given every day of said sixty (60)-day treatment period, or every other day of said sixty (60)-day treatment period, or every third day, or every fourth day, or every fifth day, or every sixth day, or every tenth day or on Day 1 and Day 30, or on Days 1, 10, 20, 30, 45, 60, of said sixty (60)-day treatment period. It may be more desirable to give a phosphonate for the first week at one dose, then switch to other doses for the second, third, and/or fourth weeks. It may be desirable to administer one type of phosphonate on some treatment days, and another type on another treatment day. It may also be desirable to administer the same or different phosphonates on different days of the treatment period. The only limitation is that the phosphonate must be given at a dosage systemic level of 0.0005 mgP/kg–1.0 mgP/kg per day on at least one day of said sixty (60)-day treatment period. As long as the phosphonate is given at a systemic level of 0.0005 mgP/kg–1.0 mgP/kg per day, it may be given at a different dose within the 0.0005 mgP/kg–1.0 mgP/kg range on different days, so long as it is given at some dose within this range on at least one day of said sixty (60)-day treatment period.

As stated above, the absorption of an orally administered phosphonate compound is only about 1% to about 5% of the dosage administered. Accordingly, to achieve an oral dosage equivalent to a systemic level of 0.0005 to 1.0 mgP/kg, the oral dose must be increased twenty- to one-hundred-fold.

These sixty (60)-day treatment periods are preferably utilized sequentially, one after the other, and preferably individually tailored and designed considering the changes in the patient's conditions and needs. The preferred end point is achieving reduction in the dosage of NSAIDs, while the incidence of flares is lowered, and inflammation and pain are under control. Illustrative, but non-limiting, examples of the treatment periods possible according to the methods of this invention are described herein:

1) Indomethacin is administered at a level of about 40 mg per day for every day of said sixty (60)-day treatment period; every other day of said sixty (60)-day treatment period (on days 1, 3, 5, 7, etc.) Risedronate is administered at a systemic level of about 0.005 mgP/kg per day.

2) Risedronate is administered at an oral dose of about 0.12 mgP/kg per day for twenty (20) days; on the sixth (6th) day Piroxicam is administered at a dose of 10 mg per day for fifteen (15) days; on the twenty-first (21st) day Risedronate is again administered, but at an oral dose 0.006 mgP/kg for twenty (20) days, and on the twenty-sixth (26th) day Ibuprofen is administered at 100 mg daily for fifteen (15) days. The first twenty (20)day period is continued with Piroxicam (to bring the total to 60 days).

3) Risedronate is administered at a systemic level of about 0.002 mgP/kg per day for twenty (20) days; on the twenty-first (21st) day Naproxen is administered at a dose of 200 mg per day for fourteen (14) days, and then on day 41, Naproxen is discontinued and Risedronate is given every other day at 0.003 mgP/kg, e.g. days 41, 43, 45, . . . 59, to complete the sixty (60) day period.

4) Piroxicam is administered for thirty (30) days at a level of about 15 mg per day, and on days 31–60, no NSAID is given; on the fifth (5th) day Risedronate is administered at an oral dose of about 0.12 mgP/kg per day for thirty days, on every fifth (5th) day, i.e. on days 35, 40, 45, 50, 55 and 60.

5) Ibuprofen is administered daily for sixty (60) days at a level of 100 mg per day; on every second day, Risedronte is administered at an oral dose of 0.12 mgP/kg per day.

6) Indomethacin is administered at a level of about 100 mg per day for twenty-eight (28) days; and on every seventh (7th) day Risedronate is administered at an oral dose of 0.2 mgP/kg per day; after day 28, no NSAID is administered unless there is a flare period.

7) Risedronate is administered at an oral dose of about 0.10 mgP/kg per day for thirty (30) days, and Piroxicam is given at 15 mg per day on these same thirty days; on the thirty-first (31st) day Ibuprofen is administered every other day at a level of 100 mg/kg per day for the remainder of the treatment period; also on day 31, the Risedronate dose is lowered to an oral dose of 0.06 mgP/kg per day for the remainder of the treatment period.

8) Risedronate is administered every other day at an oral dose of about 0.02 mgP/kg per day for seven (7) days, and on every day, Naproxen is administered at a dose of about 500 mg per day until Day 30; beginning on Day 30 the Risedronate is administered every four days at an oral dose of about 0.1 mgP/kg per day; and Naproxen is administered at an oral dose of 300 mg/kg per day every other day.

9) Piroxicam is administered at an oral dose of about 15 mg per day for thirty (30) days; Risedronate is administered at an oral dose of about 0.1 mgP/kg per day, and Piroxicam is given every day at a dose of 5 mg per day, beginning on day 31.

The terms "low potency", "medium potency", and "high potency" are used to describe the bone antiresorptive capacity of the phosphonate. For example, low potency phosphonates have an LED of 1.0–0.5; medium potency phosphonates have an LED of 0.5–0.03, and high potency phosphonates have an LED of greater than 0.03–0.0001.

The potency of a particular phosphonate can be expressed in terms of its "LED" or "least effective dose", which is the minimum dose of phosphonate expressed in mg P/kg that is effective, by itself, to cause a significant inhibition of bone resorption. The specific LEDs of the phosphonates will vary depending upon their chemical composition, and their method of administration (i.e., oral or parenteral). The lower the LED, the more potent the anti-resorptive activity of phosphonate and, generally, it is desirable to administer the high potency phosphonate in lower doses and on a fewer number of days in said sixty (60)-day treatment period. Likewise, the higher the LED, the less potent the anti-resorptive activity of the phosphonate and, generally, it is desirable to administer the low potency phosphonate in higher doses and on a greater number of days in said sixty (60)-day treatment period. However, some phosphonates, particularly sulfur-containing phosphonates, show exceptional efficacy in treating arthritis even at low doses given on relatively few days, despite the fact that their LED (as related to anti-resorptive activity) would indicate that they should be given at higher doses on a greater number of days.

In particular, the LEDs for the bone-active phosphonates may be determined using any of several art-recognized in vivo models. One such model is the thyroparathyroidectomized ("TPTX") rat model. In this model, compounds are evaluated for in vivo bone resorption inhibition potency, by measuring their ability to inhibit the increase of serum calcium levels caused by administration of NSAIDS in rats whose parathyroid gland has been removed. This model is described in Russell et al., 6 *Calcified Tissue Research* 183 (1970); Muhlbauer et al., 5 *Mineral Electrolite Metabolism* 296 (1981); U.S. Pat. No. 4,761,406, Flora et al., issued Aug. 2, 1988; and European Patent Publication 298,553, Ebetino, published Jan. 11, 1989; all of which are incorporated by reference herein.

Another model is the "Schenk Model", which measures the effects of bone-active phosphonates on bone growth in young rats. This model is described in Schenk et al., 11 *Calcif. Tissue Res.* 196 (1973); Shinoda et al., 35 *Calcif. Tissue Int.* 87 (1983); U.S. Pat. No. 4,761,406, Flora et al., issued Aug. 2, 1988; and European Patent Publication 298, 553, Ebetino, published Jan. 11, 1989; all of which are incorporated by reference herein.

Another model is the "ovariectomized" or "OVX" rat model, which measures the ability of bone-active phosphonates to prevent estrogen-deficient loss of bone in female rats induced by ovariectomy. This model is described in Wronski et al., 125 *Endocrinology* 810 (1989), incorporated by reference herein.

Another model is the "Adjuvant Model" which induces arthritis in the Lewis rat using Mycobacterium butyricum. This model in a number of ways mimics rheumatoid arthritis in the human and exhibits joint swelling associated with cellular and pannus invasion of the joint space, bone resorption, and release of chemotactic factors and lysosomel constituents into the joint space. This model is described in greater detail in Pearson et al, *Arth. Rhem.*, Vol. 2, pp. 440–59 (1959) and in Blackman, et al., *Agents and Actions*, Vol. 7, pp. 145–51 (1977). Anti-arthritic efficacy can be measured as a reduction in paw volume, body weight loss, bone loss, or reactive new bone formation compared to controls. Treatment can be stopped and the "flare" response (rapid increase in inflammation) examined which indicates a compound's ability to maintain efficacy for considerable lengths of time without additional treatment.

The LEDs for systemic dosing of preferred bone-active phosphonates useful herein are: 0.0003 mgP/kg for 2-(3-pyridinyl-1-hydroxyethylidene-bisphosphonic acid; 0.01 mgP/kg for 3-(2,2-diphosphonoethyl)-1-(2-mercaptoethyl) pyridinium chloride; 0.01 mgP-kg for 3-(2,2-diphosphonoethyl)-1-methylpyridinium chloride; and 0.001 mgP/kg for 3-(2-Hydroxy-2,2-diphosphonoethyl)-1-methylpyridinium Iodide disodium salt.

The LEDs for oral dosing would be higher, depending upon the systemic absorption of the phosphonate. Typically, absorption from oral administration is from about 1% to about 5%. Thus, oral LEDs are typically about twenty- to one hundred-fold higher than the systemic LEDs.

As used herein, the term "mg P/kg" refers to the amount of compound, expressed as milligrams phosphorus in the compound, per kilogram weight of the subject to be treated. Because the phosphonates vary in molecular weight, expressing the amount administered in mg P/kg normalizes the comparison between phosphonates of varying potencies. In order to determine the mg P/kg administered to a patient according to the methods of this invention, the following conversion formula is used:

$$\text{mg/kg compound administered} = \frac{\text{mg }P}{\text{kg}} \times \frac{\text{molecular weight of the drug}}{\text{molecular weight of two phosphorus atoms}}$$

For example, 2-(3-pyridinyl)-1-hydroxyethylidene-1,1-bisphosphonate has a molecular weight of 350. Two phosphorus atoms have a molecular weight of 62. Thus, if a patient is systemically dosed at a level 0.01 mg/kg of the compound, then about 0.002 mg P/kg was administered.

NSAIDS are routinely dosed in mg/kg or mg, and the total daily dosage is usually reported.

The methods of this invention comprise treatment of arthritis at all stages of the disorder. Since arthritis is an ongoing and progressive process of bone and joint destruction and inflammatory responses rather than a disorder having a discrete beginning- or end-point, "treatment", as referred to herein, consists of any method which stops, slows, inhibits or reverses the process of bone and joint destruction and/or relieves inflammatory symptoms which occurs in arthritis and/or which prevents and/or reduces the incidence of active flare periods.

Preferred methods of this invention comprise treatment of arthritic patients before significant joint and bone damage has occurred. Ideally, at the first sign of joint pain, inflammation, or impaired range of motion, and before significant joint or bone damage occurs or there is evidence of a flare period, an arthritic patient would be started on phosphonate therapy. If started early enough in the arthritic disease process, the phosphonate therapy would greatly reduce (or even halt) the amount of intra-articular joint damage which would be suffered during the progression of the disease; perhaps a patient started on phosphonate early enough in the disease process would never suffer a severe flare. This type of individual would ideally be identified by some serum or genetic marker; however, at the first pain in a digit or fleeting bone and/or joint pain, swelling, stiffness, or impaired range of joint motion, phosphonate therapy would ideally be started. This initial phosphonate therapy would consist of a loading period where a low to moderate dose of phosphonate would ideally be given daily for a period of two weeks to three months, depending upon the condition of the particular patient.

However, it will most generally be the case that a patient will not seek treatment from a physician until symptoms of pain and inflammation have persisted for some prolonged period of time and/or one or more acute flares have developed. These patients may have suffered a considerable amount of bone damage and will need to be administered a phosphonate compound at relatively high doses as described herein for some period of time in order to inhibit intraarticular joint or bone damage, and allow subchondral bone repair. If this patient presents with current inflammation and/or edema, it may also be desirable to administer NSAIDs at conventionally therapeutic doses to relieve the inflammation and/or edema. Once inflammation and/or edema has stabilized, then the therapeutic regimens described herein can be instituted, dosing the phosphonate compound at the higher end of the dosage range and the NSAID at the maintenance levels described herein, but at a dose high enough to alleviate flare periods and keep inflammation and edema under control.

The specific period of time sufficient to achieve a maintenance therapy with the lowest possible dosage of NSAID possible, while maintaining flare-free periods for as long as possible in the patient, may depend on a variety of factors. Such factors include, for example, the specific actives employed, the amount of actives administered, the age and sex of the subject, the specific disorder to be treated, concomitant therapies employed (if any), the general physical health of the patient (including the presence of other disorders), the extent of bone and joint damage in the individual, and the nutritional habits of the individual.

The therapeutic treatment regimens utilizing the methods of this invention are preferably continued for at least about twelve months, and generally it is preferred that maintenance therapy be continued for the life of the patient. The preferable treatment regimen is one that minimizes NSAID dose, reduces phosphonate dose, and still preserves intraarticular joint integrity, controls pain, inflammation, and edema, and/or alleviates or prevents flares. Of course, a therapeutic regimen may be continued indefinitely, according to sound medical practice.

In the methods of this invention, "administering" refers to any method which, in sound medical practice, delivers the actives used in this invention to the patient to be treated in such a manner so as to be effective in the building of bone. The actives may be administered by any of a variety of known methods of administration, e.g., orally, dermatomucosally (for example, dermally, sublingually, intranasally, and rectally), systemically (i.e. parenterally, for example, by subcutaneous injection, intramuscular injection, intra-articular injection, intravenous injection), and by inhalation. Thus, specific modes of administration include, but are not limited to, for example, oral, transdermal, mucosal, sublingual, intramuscular, intravenous, intraperitoneal, subcutaneous administration, and topical application. No matter what route of administration is utilized the phosphonate active agents must be administered in a dose equivalent to a systemic level of 0.0005 mgP/kg to 1.0 mgP/kg. Since absorption is only 1% to 5% when the phosphonate is administered orally, the oral dose to achieve a desired systemic level must be increased twenty- to one hundred-times the systemic level desired.

There are other therapies in addition to NSAIDs used in the treatment of arthritis including, but not limited to, corticosteroids, immunosuppressants, and disease modifying arthritic agents (hereinafter DMARDs) including gold, methotrexate, azathioprine, cyclosporin-A, penicillamine, and cyclophosphamide. While most patients who visit their physician are first prescribed NSAIDs due to the undesirable side effects and inconveniences of the above-described therapies, many patients will subsequently be put on a treatment regimen consisting of, for instance, NSAIDs and an occasional cortisone injection, or NSAIDs and gold or methotrexate injections. While the needs of the individual patient must be assessed by the physician, it is believed that many patients who need one or more of the above-described therapies in addition to NSAID therapy can be improved with the administration of the phosphonate compound to the point that, ultimately, therapy with corticosteroids, immunosuppressants, and DMARDs will not be necessary. It is believed that once the patient is administered NSAIDs and phosphonates for a period and stabilized, therapy utilizing those additional agents will not be necessary. After the inflammation and pain has been alleviated and the patient's condition has stabilized, reduction may begin in the daily dosage of NSAIDs and/or the days upon which NSAIDs are dosed. It is necessary that the physician monitor the condition of the patient and not reduce the dosing of NSAIDs to the point that inflammation is not relieved and flares are not prevented. It is during flare periods, when inflammation is greatest and pain is most severe that it is thought that most damage to the intraarticular bone and hard tissue is suffered; accordingly, reducing inflammation and avoiding recurrence of flares is of primary importance.

A preferred method for the treatment of arthritis includes an initial diagnostic step, to determine the presence of the disorder. Thus, a preferred method of this invention comprises the steps of performing a diagnostic on a human subject for the detection of arthritis and, upon obtaining a positive result from said diagnostic, administering the actives according to the methods of this invention. Such methods of arthritis diagnosis are well known in the art, and include clinical evaluation and/or observation, joint swelling and deformity, X-ray, erythrocyte sedimentation rate, radiographs, rheumatoid factor, C1q Antibody levels, IgG glycosalation, soluable IL-2 receptor levels, magnetic resonance imaging (MRI), and synovial neopterin levels.

Dosage Forms:

The bone-active phosphonate and NSAID may be administered in any of a variety of pharmaceutically-acceptable compositions. Such compositions may comprise an active(s) and a pharmaceutically-acceptable excipient. Pharmaceutically-acceptable excipients include solid or liquid filler diluents or encapsulating substances, and mixtures thereof, that are suitable for administration to a human or other animal. The term "compatible", as used herein, means that the components of the pharmaceutical composition are capable of being commingled with the actives, and with each other, in a manner such that there is no interaction which would substantially reduce the pharmaceutical efficacy of the pharmaceutical composition under ordinary use situations. Pharmaceutically-acceptable excipients must, of course, be of sufficiently high purity and sufficiently low toxicity to render them suitable for administration to the human or other animal being treated.

Some examples of the substances which can serve as pharmaceutical excipients are: sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and actives may be included in the pharmaceutically-acceptable excipients for use in the compositions of the present invention.

The choice of a pharmaceutically-acceptable excipient to be used in conjunction with the active is determined by the way the active is to be administered. If the active is to be injected, the preferred pharmaceutical excipient is sterile water, physiological saline, or mixtures thereof. The pH of such parenteral composition is preferably adjusted to about 7.4. Suitable pharmaceutically-acceptable excipients for topical application include those known in the art for use in creams, gels, tapes, patches, and similar topical delivery means.

The pharmaceutically-acceptable excipient employed in conjunction with the actives is used at a concentration sufficient to provide a practical size to dosage relationship. The pharmaceutically-acceptable excipients, in total, may comprise from about 0.1% to about 99.9% by weight of the pharmaceutical compositions for use in the methods of the present invention, preferably from about 5% to about 80%, and most preferably from about 10% to about 50%.

A preferred method of administering phosphonates and NSAIDS is orally, in a unit-dosage form (i.e., a dosage form containing an amount of active suitable for administration in one single dose, according to sound medical practice). Preferred unit dosage forms for phosphonate include tablets, capsules, suspensions, and solutions, comprising a safe and effective amount of active. Pharmaceutically-acceptable excipients suitable for the preparation of unit dosage forms for oral administration are well known in the art. Their selection will depend on secondary considerations like taste, cost, shelf stability, which are not critical for the purposes of the present invention, and can be made without difficulty by a person skilled in the art.

Oral unit dosage forms of the bone-active phosphonate comprise the equivalent of from about 0.0005 mgP/kg systemic per day to about 1.0 mgP/kg systemic per day of the phosphonate. As stated hereinabove, to achieve a desired systemic level, the amount of phosphonates necessary for oral dosing is higher than the systemic dose and depends upon the systemic absorption of the phosphonate. Generally oral doses are about twenty- to one hundred-fold higher than systemic doses for a particular desired systemic level.

Preferably, oral units of NSAIDS comprise from 20%–80%, more preferably 20–70%, most preferably 20–50% of the conventional therapeutic dosage for the particular NSAID. Dosages vary for particular NSAIDs and are usually reported in oral doses in mg/day or mg-kg/day.

Kits:

This invention also provides kits for conveniently and effectively implementing the methods of this invention. Such kits comprise one or more unit doses of bone-active phosphonate, one or more unit doses of NSAIDs, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means includes instructions, packaging, and dispensing means, and combinations thereof. Examples of packaging and dispensing means are well known in the art, including those described in U.S. Pat. Nos. 4,761,406, Flora et al., issued Aug. 2, 1988; and 4,812,311, Uchtman, issued Mar. 14, 1989 and 4,833,125, Neer et al., issued May 23, 1989, all incorporated by reference herein.

The following non-limiting examples illustrate the compositions, processes and uses of the present invention.

EXAMPLE A

A Caucasian male, weighing approximately 92 kilograms, seventy-two years of age, is suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. His right knee is severely inflamed and swollen and his pain is especially severe. He returns to his physician who then prescribes 20 mg of Piroxicam daily for a period of thirty (30) days. At the end of the 30 day period, the inflammation and swelling has subsided. The physician then prescribes the following therapeutic regimen for sixty (60) days: 15 mg Piroxicam daily and 60 mg daily of Risedronate orally each day for an oral dose of 0.13 mgP/kg. His clinical symptoms of pain and swelling, particularly with extended walking, improved significantly after his 2 months of therapy. At the conclusion of those two months, the physician prescribed the following regimen for six-months 50 mg Ibuprofen once every other day and Risedronate orally once weekly at 30 mg per day.

EXAMPLE B

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA), she is diagnosed with rheumatoid arthritis.

After unsuccessful analgesic and anti-inflammatory therapy, her physician prescribes Risedronate orally at 35 mg daily and Indomethacin at 50 mg daily for a period of four months. After a month of therapy, her symptom of knuckle swelling noticeably improves and her range of finger motion increases significantly and she continues therapy for the remainder of the four months. Her physician then reduces the dose of Indomethacin to 30 mg per day and the Risedronate to 15 mg per day orally for two months. After the two month period, she has no significant flaring, so her physician prescribes a maintenance therapy for six months consisting of Risedronate orally at 15 mg per day, administered once weekly, and Ibuprofen daily at 100 mg per day.

EXAMPLE C

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of a solution containing 7 mg Risedronate, daily, over a period of six days, at the rate of 1 injection per day, administered over two hours. At the conclusion of the IV regimen, the physician prescribes Risedronate at a daily oral dosage of 16 mg/day and Naproxen at a daily dosage of 400 mg/day, for a sixty (60) day period, during which she exhibits marked improvement with increased mobility and decreased pain. For the succeeding two months, the physician reduces her Risedronate dose to ¾ of the original oral dose and reduces her Naproxen dose to 200 mg/day. At the conclusion of this regimen, the daily Risedronate dosage is again reduced to ¼ of the original oral dose, her Naproxen is discontinued, and her physician prescribes 50 mg Ibuprofen per day.

EXAMPLE D

A human female patient weighing 70 kg with fulminating rheumatoid arthritis involving the knee joints is treated by this invention as follows:
1) Administration of Indomethacin capsules orally at 50 mg 2x/day for 2 weeks then the dose is dropped to 25 mg 2x/day for 4 weeks, and finally to 10 mg 2x/day for an additional 2 weeks, to bring soft tissue inflammation and discomfort to a minimum. Indomethacin is then discontinued until a flare is manifested again at which time this regimen is repeated.
2) Risedronate is administered orally once/day at 0.1 mgP/kg for 70 days (10 weeks) beginning therapy at the same time as initiating the NSAID therapy. Thereafter, all treatment is stopped until a flare of inflammation is encountered at which time the Risedronate regimen is repeated. If no flare is encountered after 3 months off all treatment, Risedronate treatment should be reinitiated to prevent the onset or recurrence of the disease process at a daily capsule dose of 0.05 mgP/kg for 60 days. Thereafter dosage can be discontinued indefinitely unless a flare of inflammation occurs.

EXAMPLE E

A human female patient with established rheumatoid arthritis of the hand and wrist, but quiescent (not in flare) is treated by this invention as follows:
1) Oral Naproxen tablets at 300 mg 1x/day for 4 weeks then treatment is stopped. Naproxen will be discontinued indefinitely unless a flare occurs at which time Naproxen treatment will be resumed at 200 mg 2x/day for 4 weeks and then discontinued.
2) Treat patients daily with 3-(2,2-diphosphonoethyl)-1-methyl-pyridine chloride tablets at 0.1 mgP/kg per day indefinitely.

EXAMPLE F

A male East Indian patient weighing 60 kg with an established history of arthritic flares in the hip, but currently in apparent complete remission is treated by this invention as follows:
1) Patient will receive no NSAID.
2) Patient will receive 2-mercapto-ethane 1,1-diphosphonate (HSEDP) for 3 months to block the onset of a flare and then go off treatment. If examination of the flare history indicates the minimum time between flares is 2 months, HSEDP should be reinitiated after 3 months at the above dosage regimen. If after 4 cycles of the above (2 yrs.) no flare has occurred, then stop phosphonate treatment indefinitely until a flare occurs. At this occurrence the patient is placed on NSAID (Voltaren) simultaneous with HSEDP, at 50 mg Voltaren 3x/day and 300 mg HSEDP 1x/day orally until flare subsides, then discontinue Voltaren and continue treatment of HSEDP for a total of 3 months.

EXAMPLE G

An elderly male ex-athlete with severe osteoarthritis of the knees is treated by the following invention:
1) The patient is dosed with 1000 mg Motrin caplets for 14 days and then the dose is dropped to 500 mg for 2 weeks, then to 500 mg every other day for 4 weeks, and then stopped. No further dosing with an NSAID is necessary, unless an injury or spontaneous swelling occurs, at which time Motrin is reinstituted at 500 mg 2x/day for 14 days and then the medication is stopped. Again if no swelling but pain is encountered with the patient, dosing with Motrin is instituted at 50 mg/day for 3 weeks and then terminated In the event of an unexpected swelling to the knee joint, treatment would be reinstituted at 1000 mg Motrin as described above.
2) The patient is treated with an oral dose of 30 mg/day of 3-(2,2-diphosphphonoethyl)-1-methyl pyrindium chloride for 4 weeks beginning at the same time as the NSAID and then the dose is dropped to 20 mg/day orally for an additional 6 weeks.

EXAMPLE H

An Afro-American patient with osteoarthritis of the left hip encountering severe pain at night and movement debility and pain during the day is treated according to the following invention:
1) An initial regimen of 15 mg Feldene is begun and maintained for 4 weeks. At this time, therapy with Feldene is dropped to 5 mg 2x/day for an additional four weeks and then treatment is stopped. No further NSAID therapy is necessary unless a flare, due to injury, is encountered, and then the above regiment is reinitiated.
2) The patient is started on 2-mercaptoethane-1,1-diphosphonate (HSEDP) at 500 mg/day for 60 days and then the treatment is stopped for 30 days, reinitiated at 500 mg/day for 1 month.

Then the dose is stopped for 30 days and then the patient is maintained on HSEDP for 1 year at a dose of 600 mg 1x per week. In the event of a flare and/or pain in the hip due to an accidental injury, the above regimen is reinitiated.

What is claimed is:

1. A method for treating a human or other animal subject afflicted with arthritis comprising at least one sixty (60)-day treatment period, comprised of an NSAID administration regimen and a bone active phosphonate administration regimen, wherein
   (a) said NSAID administration regimen is administered during a flare episode which comprises the administration to said subject of NSAIDs at a dose of from 20% to 80% of the conventionally prescribed daily dose on each day that said NSAID is administered; provided that said NSAID is administered in sufficient quantities and on a sufficient number of days to alleviate symptoms of inflammation, said NSAID selected from the group consisting of salicylates, indomethacin, flurbiprofen, diclofenac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, salidifamides, sulindac, suprofen and tolmetin, and wherein
   (b) said bone active phosphonate administration regimen comprises the administration to said subject of a bone active phosphonate, or a pharmaceutically-acceptable salt or ester thereof at a dose equivalent to a systemic level of from about 0.005mgP/kg to about 1.0 mgP/kg per day that said phosphonate is administered; provided that said phosphonate is administered at least 1 day of every sixty (60)-day treatment period.

2. A method of treating a human or other animal subject afflicted with arthritis, according to claim 1 wherein said NSAID administration regimen comprises the administration of NSAIDs at a dose of from 20% to 70% of the conventionally prescribed daily dose on each day that said NSAID is administered.

3. A method of treating a human or other animal subject afflicted with arthritis, according to claim 1 wherein said NSAID administration regimen comprises the administration of NSAIDs at a dose of from 20% to 50% of the conventionally prescribed daily dose on each day that said NSAID is administered.

4. A method of treating arthritis in a human or other animal subject afflicted with arthritis, according to claim 1, before a significant intraarticular joint or bone destruction has occurred in said subject.

5. A method of treating a human or other animal subject afflicted with arthritis, according to claim 1, wherein said bone-active phosphonate is a bisphosphonic acid, or a pharmaceutically-acceptable salt or ester thereof.

6. A method of treating a human or other animal subject afflicted with arthritis, according to claim 1, wherein said phosphonate is selected from the group consisting of:
   3-pyridyl-1-hydroxyethylide-1,1-bisphosphonic acid; 3-(2,2-Disphosphonoethyl)-1-ethylpryridinium Chloride; 3-(2,2-Diphosphonoethyl)-1-(2-mercaptoethyl) pyridinium Chloride; 3-(2-Hydroxy-2,2-diphosphonoethyl)-1-methylpyridinium Iodide pedosium salt; 3-(2-Hydroxy-2,2-diphosphonoethyl)-1-methylpyridinium Hydroxide; 2-(2-Hydroxy-2,2-diphosphonoethyl)-1-methylpyridinium hydroxide; 3-(3hydroxy-3,3-diphosphonopropyl)-1-methyl-pyridinium Hydroxide; 2-(2-hydroxy-2,2-diphosphonoethyl)-1,1-dimethyl piperidinium Iodide; 3-[2,2-Diphosphono-2-hydroxyethyl]-1,1-dimethyl piperidinium Iodide; 3-(2–Carboxy-2-phosphonoethyl)-1-methyl-pyridinium chloride; 3-(3,3-diphosphonopropyl)-1-hexadecylpyridinium; 7-diphosphonohydroxymethyl)-2-methyl-2-pyridinium iodide; Octahydro-6,6-diphosphono-1,1-dimethyl-1-pyrindinium iodide; Octahydro-6,6-diphosphono-2,2-dimethyl-2-pyrindinium iodide; Octahydro-7,7-diphosphono-1,1-dimethyl-1-pyrindinium Iodide; Dihydro-6,6-diphosphono-1-methyl-1-pyrindinium; Dihydro-6,6-diphosphono-2-methyl-2-pyrindinium; Tetrahydro-8,8-diphosphono-1-methylquinolinium Iodide; Octahydro-8,8-diphosphono-1,1-dimethylquinolinium Iodide; Dihydro-1-methyl-6-phosphono-6-sulfono-1-pyrindinium chloride; Octahydro-6,6-diphosphono-1-(2-mercaptoethyl)-1-methyl-1-pyrindinium chloride; Octahydro-6,6-diphosphono-1,1-dimethyl-3-(2-mercaptoethyl)-1-pyrindinium iodide; 1,3-dihydro-4-(2-mercaptoethyl)-2,2-diphosphono-2H-pyrrolo[3,2-b]pyridinium chloride; [(5-(3-mercaptopropyl)-2-pyridinyl)aminomethylene]bis[phosphonic acid]; [(5-(3-Acetylthiopropyl)-2-pyridinyl)aminomethylene]bisphosphonic acid]; [(5-mercapto-2-pyridinyl)aminomethylene]bis[phosphonic acid]; [(4-(4-mercaptoethyl)-2-pyridinyl)aminomethylene]bis[phosphonic acid]; [(4-(4-Acetylthiobutyl)-2-pyridinyl)aminomethylene] bis[phosphonic acid]; [[5-[(2-mercapto-1-oxopropyl)amino]-2-pyridinyl]aminomethylene]bis[phosphonic acid]; 2-[Acetylthio-2-(3-pyridinyl)ethylidene]bis[phosphonic acid]; [2-mercapto-2-(3-pyridinyl)ethylidene]bis[phosphonic acid]; 5-mercapto-2-(3-pyridinyl)pentylidene]bis[phosphonic acid]; Dihydro-7-mercapto-1-pyrindene-6,6-bisphosphonic acid; Octahydro-7-mercapto-1-pyrindene-6,6-bisphosphonic acid; Dihydro-7-(2-mercaptoethyl)-1-pyrindene-6,6-bisphosphonic acid; Octahydro-7-(2-mercaptoethyl)-1-pyrindine-6,6-bisphosphonic acid; Octahydro-3-mercapto-1-pyrindine-6,6-bisphosphonic acid; Dihydro-4-mercapto-2-pyrindine-6,6-bisphosphonic acid; Octahydro-4-mercapto-2-pyrindine-6,6-bisphosphonic acid; Dihydro-3-(4-mercaptobutyl)-1-pyrindine-6,6-bisphosphonic acid; Octahydro-3-(4-mercaptobutyl)-1-pyrindine-6,6-bisphosphonic acid; Dihydro-4-(4-mercaptobutyl)-2-pyrindine-6,6-bisphosphonic acid; Octahydro-4-(4-mercaptobutyl)-2-pyrindine-6,6-bisphosphonic acid; (1-hydroxy-(dihydro-7-mercapto-2-pyrind-7-yl)methylene]bis[phosphonic acid]; [Octahydro-4-(2-mercaptoethyl)-pyrrolo[3,2-b] pyridin-2-yl]bis(phosphonic acid]; and the pharmaceutically-acceptable salts and esters thereof.

7. A method of treating a human or other animal subject afflicted with arthritis, according to claim 6, wherein said bisphosphonic acid is 3-pyridyl-1-hydroxyethylidene-1,1-bis-phosphonic acid; 3-(2,2-diphosphonoethyl)-1-(2-mercaptoethyl) pyridinium chloride; 3-(2,2-diphosphonoethyl)-1-methylpyridinium chloride; or 3-(2-Hydroxy-2,2-diphosphonoethyl)-1-methylpyridinium; or a pharmaceutically acceptable salt or ester thereof.

8. A method of treating a human or other animal subject afflicted with arthritis, according to claim 7, wherein said phosphonate is 3-pyridyl-1-hydroxyethylidene-1,1-bisphosphonic acid, or a pharmaceutically acceptable salt or ester thereof.

9. A method of treating a human or other animal subject afflicted with arthritis, according to claim 1, wherein said bone-active phosphonate is a phosphonoalkylphosphinate, or a pharmaceutically-acceptable salt or ester thereof.

10. A method of treatment according to Claim 1 wherein said NSAID is selected from the group consisting of salicylates, indomethacin, flurbiprofen, diclofenac, naproxen, piroxicam, tebufelone, and ibuprofen.

11. A method of treating a human or other animal subject afflicted with arthritis, according to claim 1, wherein said NSAID is administered every day of said sixty (60)-day treatment period.

12. A method of treating a human or other animal subject afflicted with arthritis, according to claim 1, wherein said NSAID is administered every other day of said sixty (60)-day treatment period.

13. A method of treating a human or other animal subject afflicted with arthritis, according to claim 1, wherein said NSAID is administered every third day of said sixty (60)-day treatment period.

14. A method of treating a human or other animal subject afflicted with arthritis, according to claim 1, wherein said NSAID is administered on day 15, day 30, day 45 and day 60 of said sixty (60)-day treatment period.

15. A method of treating a human or other animal subject afflicted with arthritis, according to claim 1, wherein said phosphonate is administered every day of said sixty (60)-day treatment period.

16. A method of treating a human or other animal subject afflicted with arthritis, according to claim 1, wherein said phosphonate is administered every other day of said sixty (60)-day treatment period.

17. A method of treating a human or other animal subject afflicted with arthritis, according to claim 1, wherein said phosphonate is administered every third day of said sixty (60)-day treatment period.

18. A method of treating a human or other animal subject afflicted with arthritis, according to claim 1, wherein said bisphosphonate is administered day 15, day 30, day 45, and day 60 of said sixty (60)-day treatment period.

19. A method of treating a human or other animal subject afflicted with arthritis, according to claim 1, wherein said phosphonate is administered every other day of said sixty (60)-day treatment period, and said NSAID is administered every tenth (10th) day of said sixty (60)-day treatment period.

20. A method of treating a human or other animal subject afflicted with arthritis, according to claim 1, wherein said phosphonate is administered every third day of said sixty (60)-day treatment period, and said NSAID is administered every seventh 5 (7th) day of said sixty (60)-day treatment period.

21. A method of treating a human or other animal subject afflicted with arthritis, according to claim 1, wherein said phosphonate is administered every seventh (7th) day of said sixty (60)-day treatment period, and said NSAID is administered on days 1–7 and days 15–22 of said sixty (60)-day treatment period.

22. A method of treating a human or other animal subject afflicted with arthritis, according to claim 1, wherein said phosphonate is administered on one day every seven days of said sixty (60)-day treatment period, and said NSAID is administered every other day of said sixty (60)-day treatment period.

23. A method of treating a human or other animal subject afflicted with arthritis, according to claim 1, wherein said phosphonate is administered on days 5, 10, 15, 25, 35, 50 and 60 of said sixty (60)-day treatment period, and said NSAID is administered on one day every seven days of said sixty (60)-day treatment period.

24. A method of treating a human or other animal subject afflicted with arthritis, according to claim 1, wherein said phosphonate is administered on day 15, day 30, day 45 and day 60 of said sixty (60)-day treatment period, and said NSAID is administered every fourth (4th) day of said sixty (60)-day treatment period.

* * * * *